United States Patent
Urbon et al.

(10) Patent No.: US 9,414,802 B2
(45) Date of Patent: Aug. 16, 2016

(54) CHARGER FOR ELECTRONIC GRID HOLDERS AND DETECTORS STORED AT MOBILE RADIOGRAPHIC IMAGING APPARATUS AND METHODS FOR USING THE SAME

(75) Inventors: Michael P. Urbon, Churchville, NY (US); Dennis J. O'Dea, Farmington, NY (US)

(73) Assignee: Carestream Health, Inc., Rochester, NY (US)

( * ) Notice: Subject to any disclaimer, the term of this patent is extended or adjusted under 35 U.S.C. 154(b) by 423 days.

(21) Appl. No.: 13/455,340

(22) Filed: Apr. 25, 2012

(65) Prior Publication Data

US 2013/0064351 A1   Mar. 14, 2013

Related U.S. Application Data

(60) Provisional application No. 61/533,414, filed on Sep. 12, 2011.

(51) Int. Cl.
*H05G 1/02* (2006.01)
*A61B 6/00* (2006.01)

(52) U.S. Cl.
CPC .............. *A61B 6/56* (2013.01); *A61B 6/4405* (2013.01); *A61B 6/4233* (2013.01); *A61B 6/4283* (2013.01); *A61B 6/46* (2013.01); *A61B 6/548* (2013.01); *Y10T 29/49826* (2015.01)

(58) Field of Classification Search
CPC ......... A61B 6/4405; H05G 1/06; H05G 1/08; H05G 1/02
USPC .......................................................... 378/102
See application file for complete search history.

(56) References Cited

U.S. PATENT DOCUMENTS

| | | | |
|---|---|---|---|
| 3,610,424 A * | 10/1971 | Connan | 211/13.1 |
| 5,425,069 A * | 6/1995 | Pellegrino et al. | 378/198 |
| 2006/0034427 A1* | 2/2006 | Brooks | 378/198 |
| 2006/0261296 A1 | 11/2006 | Heath et al. | |
| 2007/0153980 A1 | 7/2007 | Butzine et al. | |
| 2009/0034688 A1* | 2/2009 | Koren et al. | 378/198 |
| 2010/0019720 A1 | 1/2010 | Liu et al. | |
| 2010/0202589 A1 | 8/2010 | Ohta et al. | |
| 2011/0286575 A1* | 11/2011 | Omernick et al. | 378/62 |
| 2011/0317816 A1* | 12/2011 | Bechard et al. | 378/98.8 |
| 2012/0045037 A1* | 2/2012 | Carmichael et al. | 378/198 |

OTHER PUBLICATIONS

Supplementary European Search Report mailed Apr. 2, 2015 for European Patent Application No. 12 831 787.2, 2 pages.

* cited by examiner

*Primary Examiner* — Hoon Song

(57) ABSTRACT

A mobile radiography apparatus has a moveable (e.g., wheeled) transport frame and an adjustable support mounted at the frame that can include an x-ray source. Embodiments of methods and/or apparatus by which mobile radiography carts can provide a charging capability for at least one radiographic detector (e.g., removed power source, detector either separately mounted at the mobile radiography apparatus or in a detector carrier (e.g., grid holder)) mounted at the mobile radiography apparatus.

13 Claims, 32 Drawing Sheets

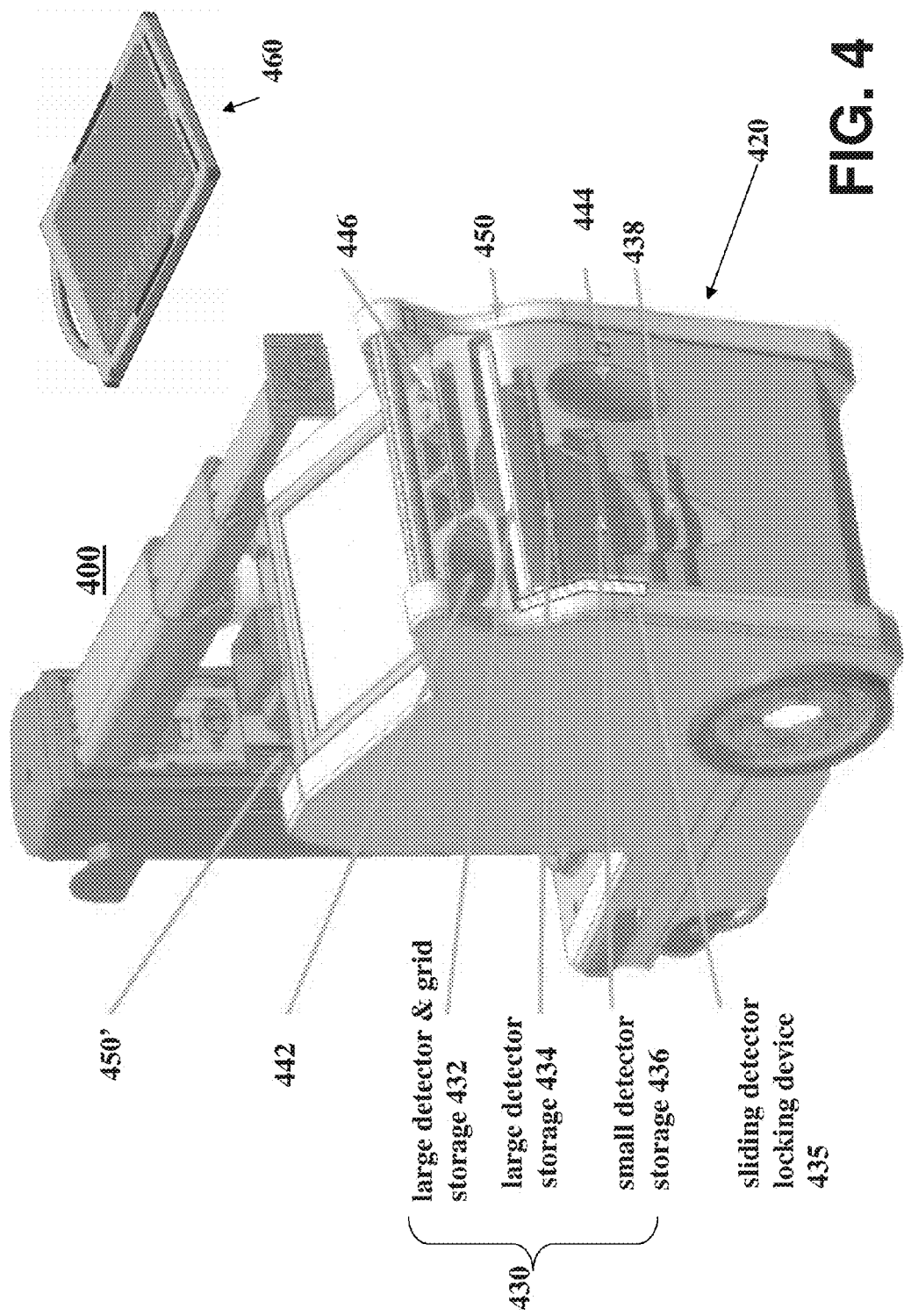

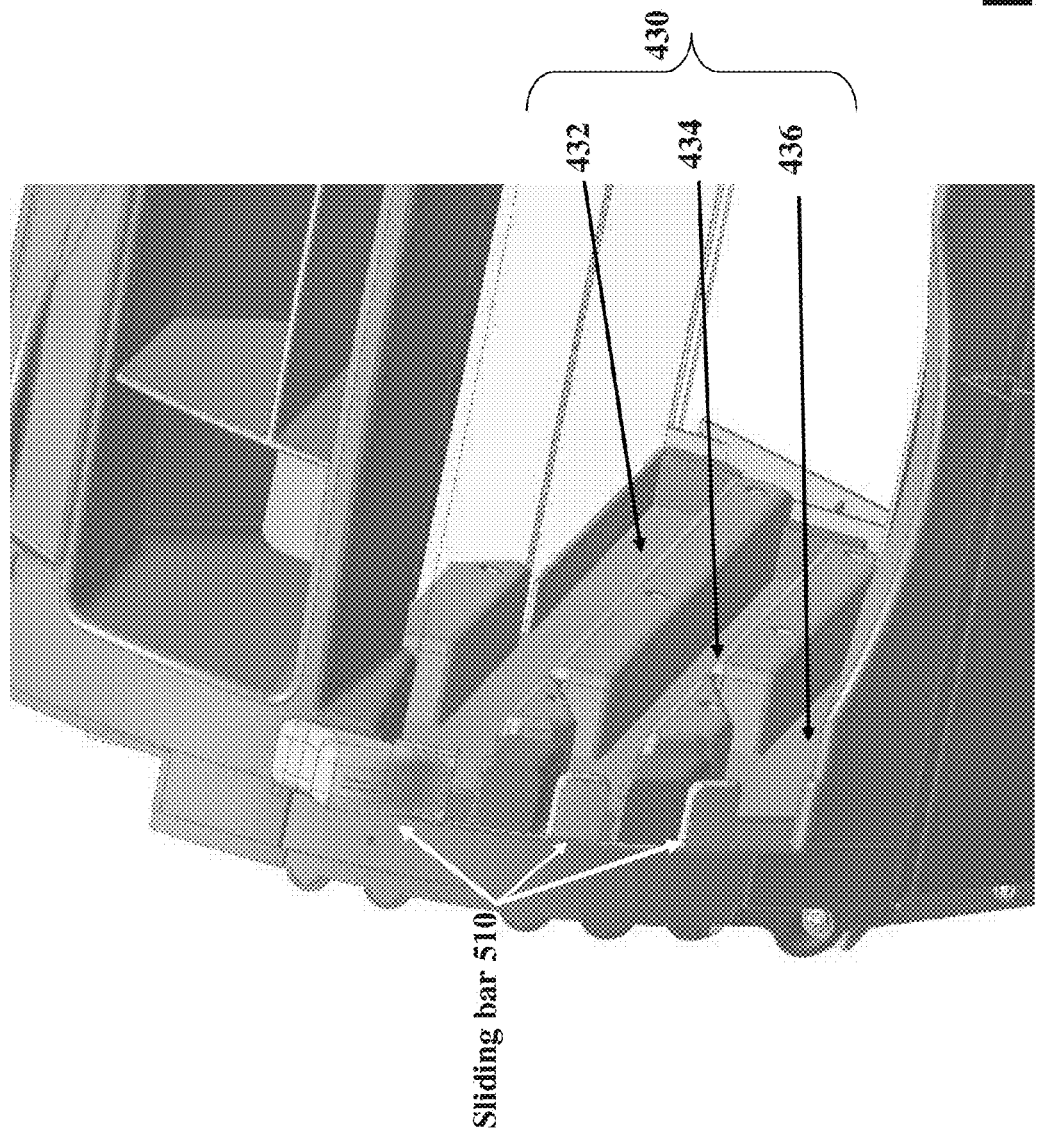

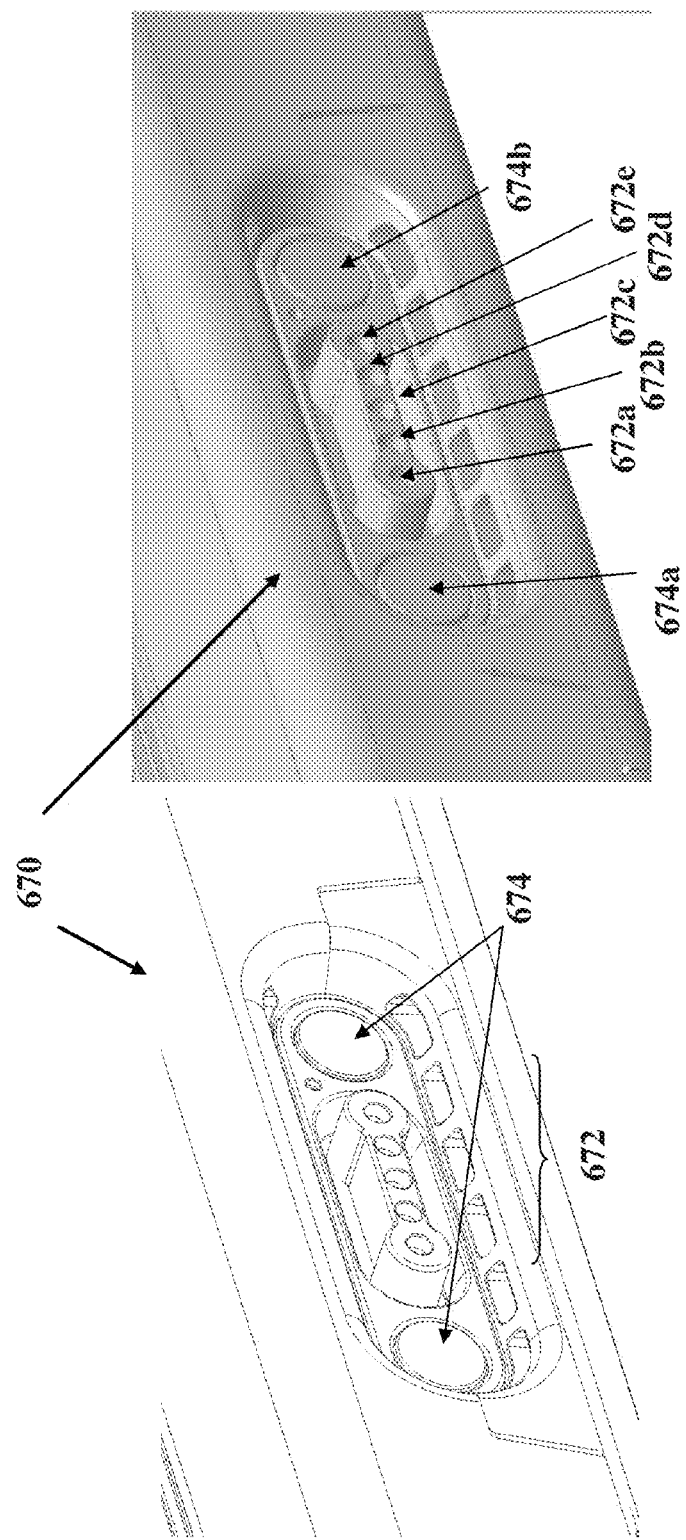

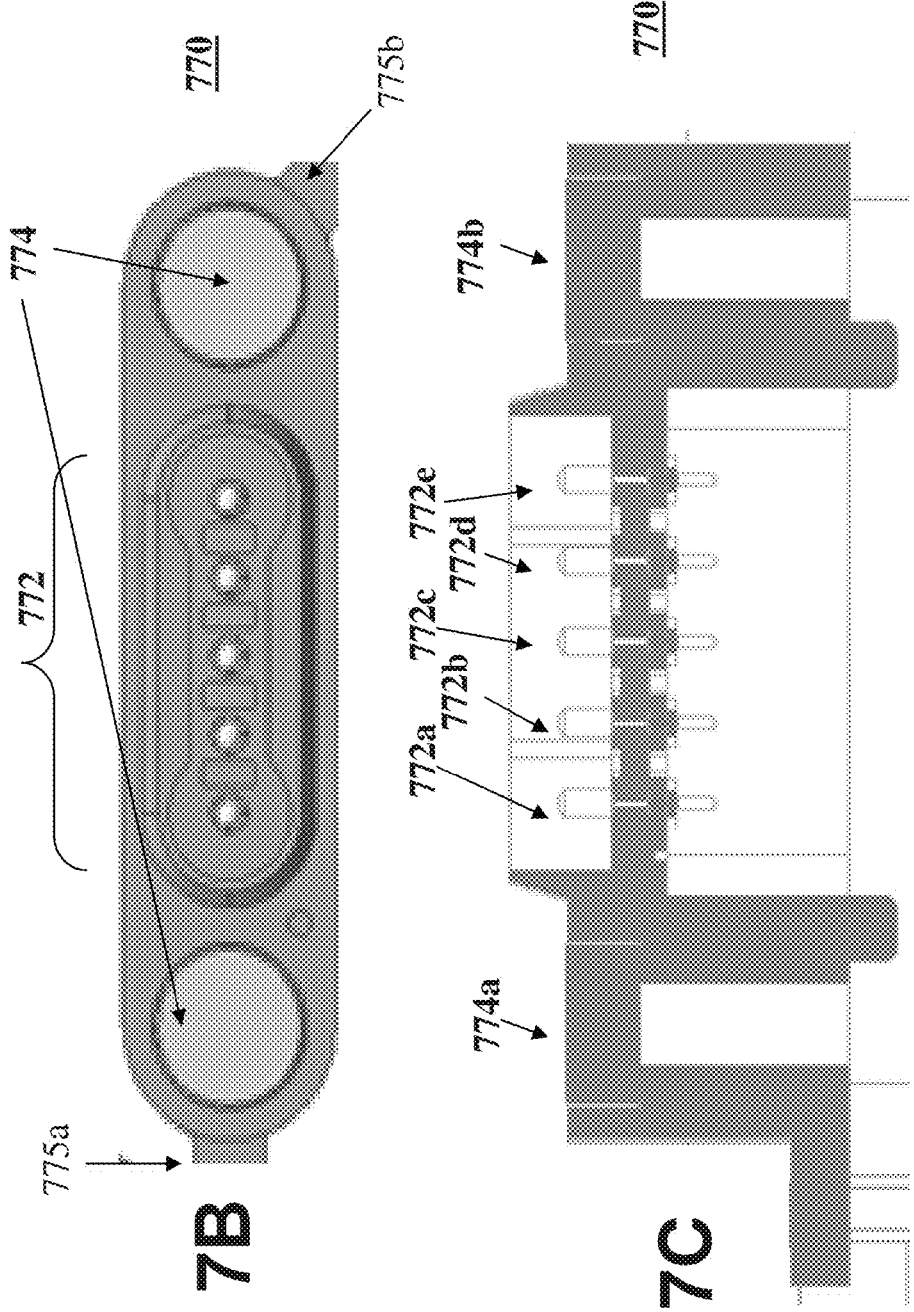

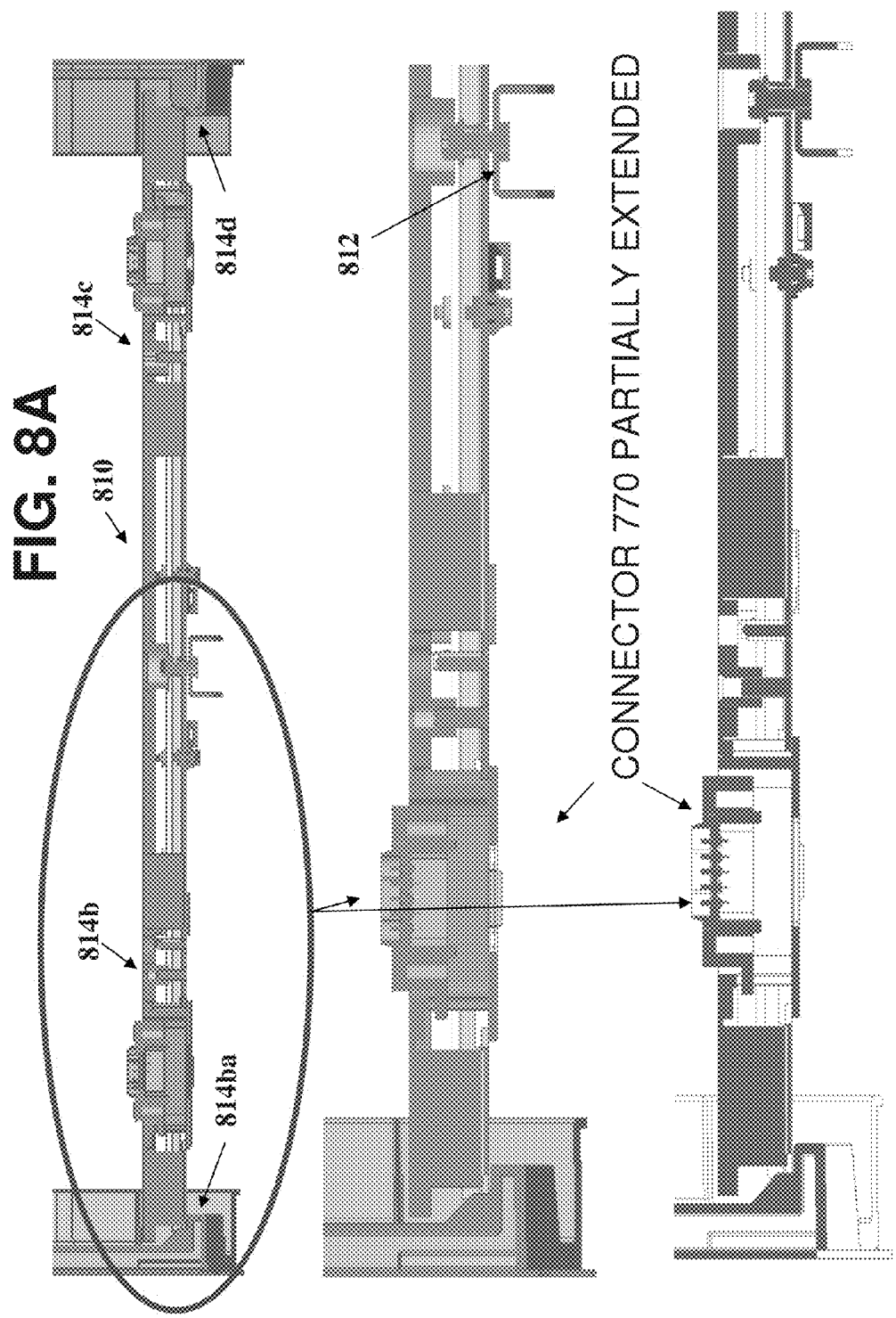

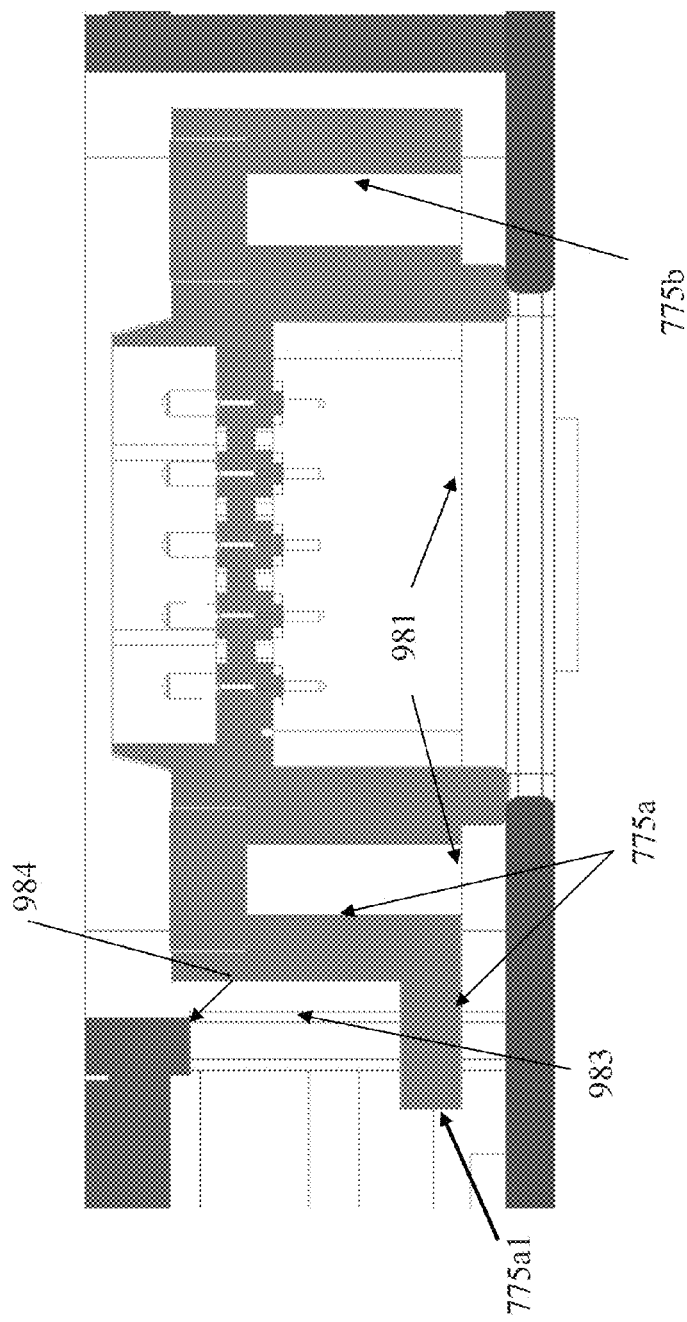

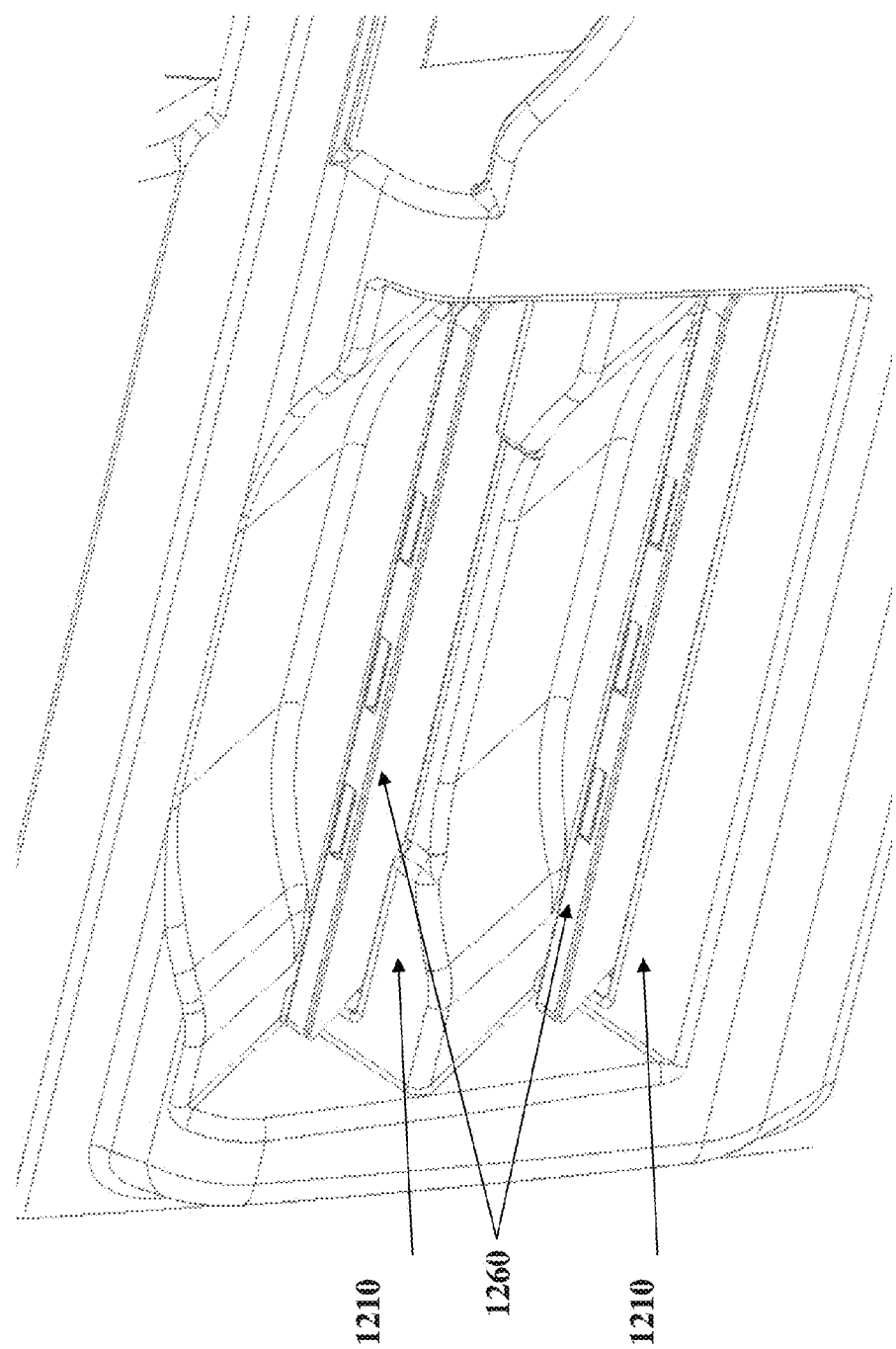

CHARGER FOR ELECTRONIC GRID HOLDERS AND DETECTORS STORED AT MOBILE RADIOGRAPHIC IMAGING APPARATUS AND METHODS FOR USING THE SAME

CROSS REFERENCE TO RELATED APPLICATIONS

Priority is claimed from commonly assigned, U.S. provisional patent applications Ser. Nos. (a) 61/533,414, filed Sep. 12, 2011, entitled "CHARGER FOR ELECTRONIC GRID HOLDERS AND DETECTORS STORED AT MOBILE RADIOGRAPHIC IMAGING APPARATUS AND METHODS FOR USING THE SAME", in the name of Michael P. Urbon et al., the disclosure of which is incorporated by reference.

FIELD OF THE INVENTION

The invention relates generally to the field of medical imaging, and in particular to portable radiographic imaging apparatus. More specifically, the invention relates to a mobile radiography apparatus including rechargeable capabilities for at least one portable radiographic detector.

BACKGROUND

Mobile carts are employed in medical facilities to move medical equipment between locations. One type of mobile cart includes an x-ray source used to capture (e.g., digital) x-ray images on x-ray detector. Medical x-ray images can be captured using various digital or analog techniques.

Mobile x-ray apparatus are of particular value in intensive care unit (ICU) and other environments where timely acquisition of a radiographic image is important. Because portable carts can be wheeled around the ICU or other area and brought directly to the patient's bedside, a portable x-ray imaging apparatus allows an attending physician or clinician to have recent information on the condition of a patient and helps to reduce the risks entailed in moving patients to stationary equipment in the radiological facility.

However, there is a need for improvements in mobile x-ray apparatus design to allow such devices to be more easily transported, deployed and/or operated.

SUMMARY

An aspect of this application is to advance the art of mobile radiography.

Another aspect of this application is to address in whole or in part, at least the foregoing and other deficiencies in the related art.

It is another aspect of this application is to provide in whole or in part, at least the advantages described herein.

Another aspect of the application is to provide methods and/or apparatus by which mobile radiography carts can be modified to provide methods for recharging and/or recharge capabilities for at least one portable radiographic detector.

Another aspect of the application is to provide embodiments of methods for recharging and/or recharge capabilities that can charge, when stored or mounted at a mobile x-ray system, at least one portable radiographic detector, at least one rechargeable power source for a portable radiographic detector, and/or at least one portable radiographic detector coupled to or mounted in a grid holder or carrier.

In accordance with one embodiment, the invention can provide a mobile radiography apparatus that can include a moveable transport frame; an adjustable support structure coupled to the moveable transport frame; an x-ray source coupled to the adjustable support structure; and at least one detector charge device configured to charge at least one portable radiographic detector at the mobile radiography apparatus. In one embodiment, a detector charge device can include at least one radiographic detector installer, where a radiographic detector installer can include a mount or a recess configured to charge a first power source for the at least one portable radiographic detector at the mobile radiography apparatus.

In accordance with one embodiment, the invention can provide a method of preparing a mobile radiography apparatus that can include providing a moveable transport frame; providing an adjustable support structure coupled to the moveable transport frame; providing an x-ray source coupled to the adjustable support structure; and attaching at least one detector recharge device configured to charge at least one portable radiographic detector at the mobile radiography apparatus.

In accordance with one embodiment, the invention can provide a mobile radiography apparatus that can include a moveable transport frame; an adjustable support structure coupled to the moveable transport frame; an x-ray source coupled to the adjustable support structure; and a detector recharge device configured to charge at least one radiographic detector at the mobile radiography apparatus, where the detector recharge device can include at least one detector mount configured to attach to the at least one radiographic detector, where the at least one detector mount comprises, at least one engaging connector configured to charge an internal power source of the radiographic detector when the radiographic detector is electrically coupled to the at least one engaging connector, and a connector housing to restrain movement of the engaging connector in at least one direction.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

FIG. 4 is a diagram that illustrates a mobile radiographic system embodiment including a securable detector storage area according to the application.

FIGS. 5A-5B are diagrams that illustrates a perspective view of an embodiment of a detector storage area for mobile radiographic system according to the application.

FIGS. 6A-6D are diagrams that illustrate an embodiments of a grid holder assembly with detector and first connector for charging at a mobile radiographic system according to the application.

FIGS. 7B-7C are diagrams that show top and side views of an exemplary connector embodiment (e.g., for use at a mount or an in-bin grid holder or the like) charging device for mobile radiographic system according to the application.

FIGS. 8A-8C are diagrams that illustrates embodiments of a connector for use at (e.g., a storage/charging slot) a mobile radiographic system according to the application.

FIG. 11 is a diagram that illustrates a perspective view of an embodiment of an in bin battery charging device including a connector for use at a mobile radiographic system according to the application.

FIG. 12A-12F are diagrams that illustrate various views of an embodiment of an in bin battery charging device including a connector for use at a mobile radiographic system according to the application.

FIGS. 14A-14B are diagrams that show various views of an embodiment of a grid holder, detector, battery storage/charging area for a mobile radiography unit according to the application.

DESCRIPTION OF EXEMPLARY EMBODIMENTS

Figure 1:
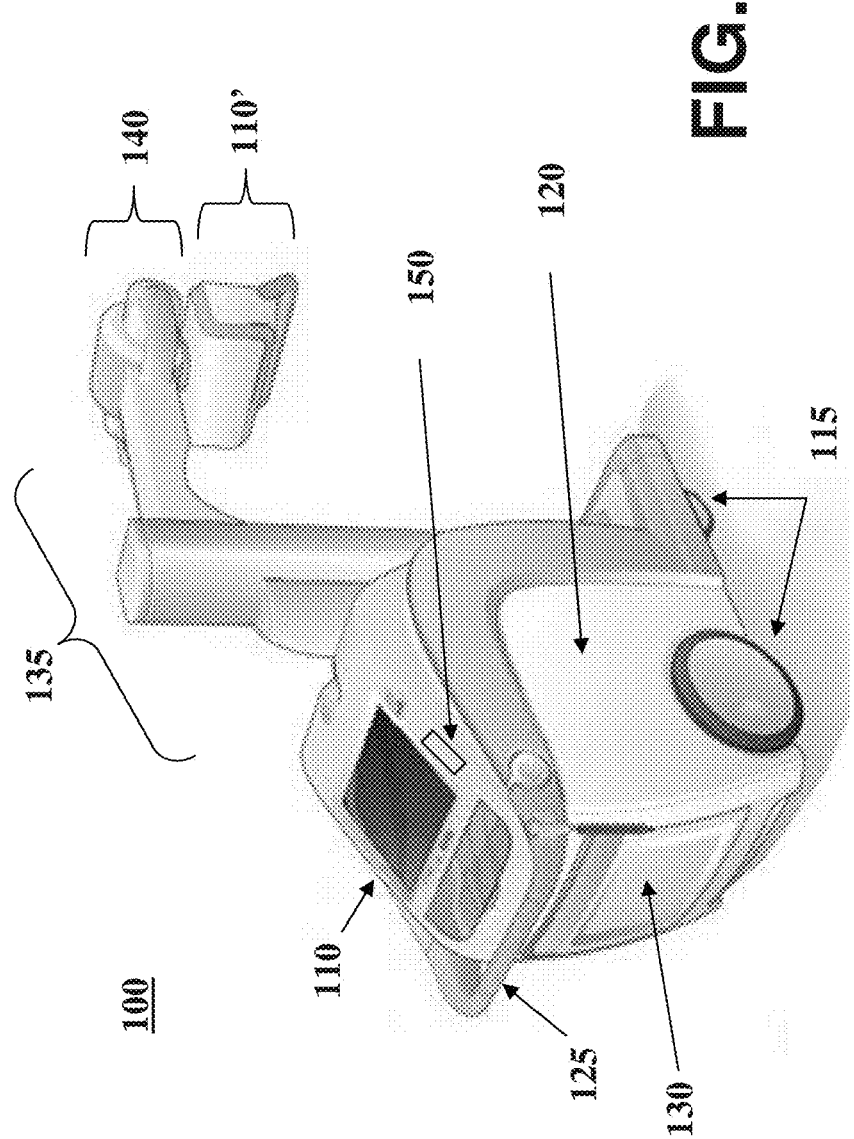
FIG. 1 is a diagram that shows a perspective view of a mobile radiography unit according to one embodiment of the application.

The following is a description of exemplary embodiments of the invention, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

FIG. 1 is a diagram that shows a perspective view of a mobile radiography unit that can include a charger for portable radiographic detectors or flat panel detectors according to embodiments of the application. The exemplary mobile x-ray or radiographic apparatus of FIG. 1 can be employed for computed radiography (CR) and/or digital radiography (DR). As shown in FIG. 1, a mobile radiography apparatus 100 can include a moveable transport frame 120 that includes a first display 110 and an optional second display 110' for display relevant information such as obtained images and related data. As shown in FIG. 1, the second display 110' can be pivotable mounted at the x-ray source 140 to be viewable/touchable from a 360 degree area.

The displays 110, 110' can implement or control (e.g., touch screens) functions such as generating, storing, transmitting, modifying, and printing of an obtained image(s) and can include an integral or separate control panel (not shown) to assist in implementing functions such as generating, storing, transmitting, modifying, and printing of an obtained image(s).

For mobility, the mobile radiographic apparatus 100 can have one or more wheels 115 and one or more handle grips 125, typically provided at waist-level, arm-level, or hand-level, that help to guide the mobile radiographic apparatus 100 to its intended location. A self-contained battery pack (e.g., rechargeable) in the frame or elsewhere can provide source power, which can reduce or eliminate the need for operation near a power outlet. Further, the self-contained battery pack can provide for motorized transport.

For storage, the mobile radiographic apparatus 100 can include an area/holder for holding/storing one or more digital radiographic (DR) detectors or computed radiography (stimulated phosphor) cassettes. The area/holder can be storage area 130 (e.g., disposed on the frame 120) configured to removably retain at least one digital radiography (DR) detector. The storage area 130 can be configured to hold a plurality of detectors and can also be configured to hold one size or multiple sizes of DR detectors or cassettes.

Mounted to frame 120 is a support column 135 that supports an x-ray source 140, also called an x-ray tube, tube head, or generator that can be mounted to the support member 135. In the embodiment shown in FIG. 1, the support member (e.g., column 135) can include a second section that extends outward a fixed/variable distance from a first section where the second section is configured to ride vertically up and down the first section to the desired height for obtaining the image. In another embodiment, the tube head or x-ray source 140 can be rotatably coupled to the support column 135. In another exemplary embodiment, an articulated member of the support column that bends at a joint mechanism can allow movement of the x-ray source 140 over a range of vertical and horizontal positions. Height settings for the x-ray source 140 can range from low height for imaging feet and lower extremities to shoulder height and above for imaging the upper body portions of patients in various positions. The mobile radiographic apparatus 100 can also include a prep/expose control 150.

Figure 2:
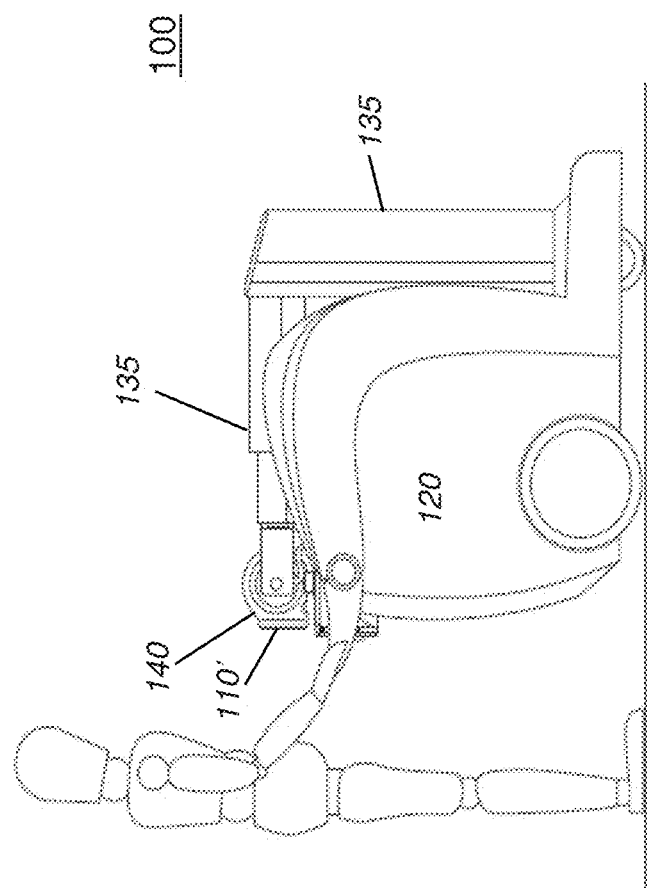
FIG. 2 is a diagram that shows a perspective view of a mobile radiography unit of FIG. 1 positioned for travel.

As shown in FIG. 2, for ease during transport of the mobile radiographic apparatus 100, the support member 135 and x-ray source 140 can be arranged close to frame 120. As shown in FIG. 2, the second display 110' can be in a viewable position (e.g., operable) during transport of the mobile radiographic apparatus 100. When the mobile radiographic apparatus 100 is to be used, the support member 135 and x-ray source 140 can be extended from the frame 120 for proper positioning (e.g., by the operator, a user, or x-ray technician) and the second display 110' moved to viewable position such as shown in FIG. 1.

Figure 3:
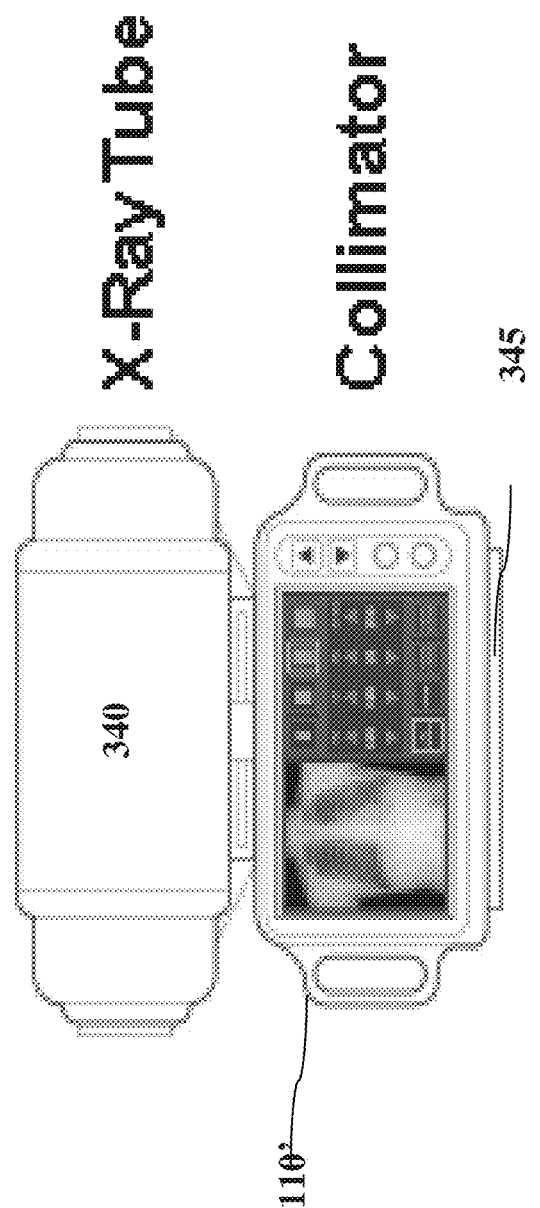
FIG. 3 is a diagram that shows an exemplary embodiment of a display/monitor as a second display mounted to a boom assembly of a mobile radiography unit according to the application.

FIG. 3 is a diagram that shows an exemplary embodiment of a display/monitor as a second display mounted to a boom assembly of a mobile radiography unit according to the application. As shown in FIG. 3, the second display 110' can be mounted to a collimator 345 of an x-ray source 340 of a support member 135 of a mobile radiography unit. In one embodiment, the collimator 345 can be rotably mounted to the x-ray source 340 so that the collimator 345 (e.g., second display 110') can swivel at least 90 degrees, at least 180 degrees or 360 degrees. As shown in FIG. 3, the second display 110' is coupled to a plurality of handles for ease of positioning. Alternatively, the second display 110' can be mounted to (e.g., rotatably) an x-ray source 340 above a collimator 345 of a boom assembly of a mobile radiography unit.

Embodiments according to the application relate to a charging device or recharging capability for a mobile radiographic system. The detector is a component that can be readily removed and/or moved to different locations preferably for repeated or continuous use or use through a full shift of a radiographic technician. Embodiments of methods for charging devices and/or chargers according to application can provide battery chargable storage for batteries within or removed from (e.g., internal or external) from portable radiographic detectors such as flat panel detectors, remote detectors, digital radiographic (DR) detectors, portable wireless DR detectors and the like that can be used with a radiographic system.

According to certain exemplary embodiments herein, each detector can be disposed in a storage area. Storage area embodiments can restrict hold, store or restrict removal of one or more radiographic detectors that have different sizes (e.g., 10 cm by 20 cm, 24 cm by 30 cm, 45 cm by 45 cm, etc.). Exemplary storage areas are shown in the figures as slots within the base of the mobile x-ray system. However, embodiments of detector storage areas are not intended to be so limited. For example, in one embodiment, the storage area can be recesses (e.g., slots, grooves, bins, mounts or the like) at or within a base, a movable bin or a fixed bin of the mobile radiographic system. Certain exemplary embodiments can provide a power source charger in at least one of the storage areas to charge a power source (e.g., battery) removed from a DR detector, a power source in a DR detector, a power source in a DR detector that is in a portable detector holder (e.g., a carrying case or a grid holder) and/or a power source provided in a detector holder.

According to exemplary embodiments, at least one detector charger can include one connector (e.g., that can be attached to a detector when stored in a storage area at the mobile x-ray system) that can move between a first detached position from an other connector, which can be securely and electrically coupled to the detector (e.g., at a DR detector or a DR detector grid holder), and extend toward variable second attached position for engagement to the other connector. An electrically path between the one connector attached to the other connector can provide a conduit to charge a remote power source (e.g., for the detector) using a power source in the mobile x-ray system.

FIG. 4 is a diagram that illustrates a mobile radiographic system embodiment including a storage area securing apparatus or a locking device according to the application. As shown in FIG. 4, a mobile radiography apparatus 400 can include a moveable transport frame 420 that includes storage area 430 and locking device 435. The storage area 430 can include a plurality of individual securable portions or slots such as detector holder storage or large detector and grid storage 432, large detector storage 434, and/or small detector storage 436 that can be secured using locking device 435. Exemplary detector holders can include a detector with/without a grid and/or additional detector accessories such as but not limited to additional antenna, power supply or additional electronics. Storable detector holders can include just the holder without the detector. The locking device 435 can reciprocally move between a first position (e.g., unlocked) where detectors can be removed from the storage area and a second position (e.g., locked) where detectors can not be removed from the storage area. In one embodiment, the storage area 430 can include an area or battery charge slots 438 where at least one battery for use with or removed from detectors 460 can be re-charged by the mobile radiography apparatus 400. Additional storage areas for materials at the mobile radiography apparatus 400 can include storage 442 (e.g., for rubber gloves), bag storage area 444, and additional storage 446. The mobile radiography apparatus 400 can also include a wired prep/expose control 450 and a remote prep/expose control 450'.

As shown in FIG. 4, a single locking device 435 can cover a left side portion of openings of three storage areas. Alternatively, the locking device 435 can be positioned along a right side or cross between left and right edges of the storage area 430 and be a contiguous integral device, a discontinuous locking device (e.g., two or more sliding members), or a plurality of sliding locking device 435, each for one or more detector storage portions such as storage 432, 434, 436.

Figure 5A:
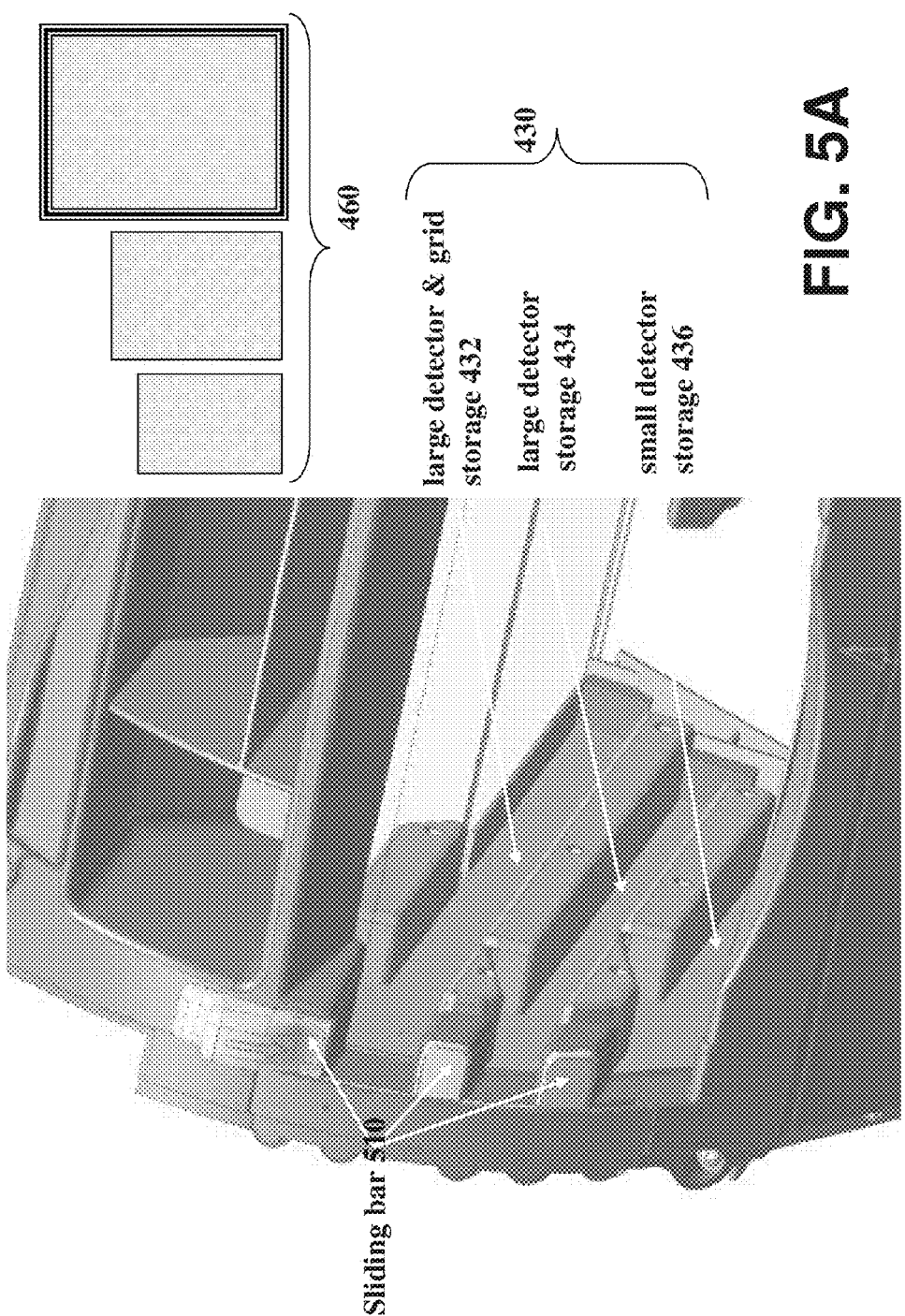

FIGS. 5A-5B are diagrams that illustrate an embodiment of a securing apparatus or a locking device for mobile radiographic system. FIG. 5A shows a sliding detector locking device in a first, open or unlocked (e.g., unengaged) position and FIG. 5B shows a sliding detector locking device in a second, closed or secured (e.g., engaged) position. In one embodiment, a securing apparatus can include a sliding lock 510 securing multiple detectors.

Figure 6A:
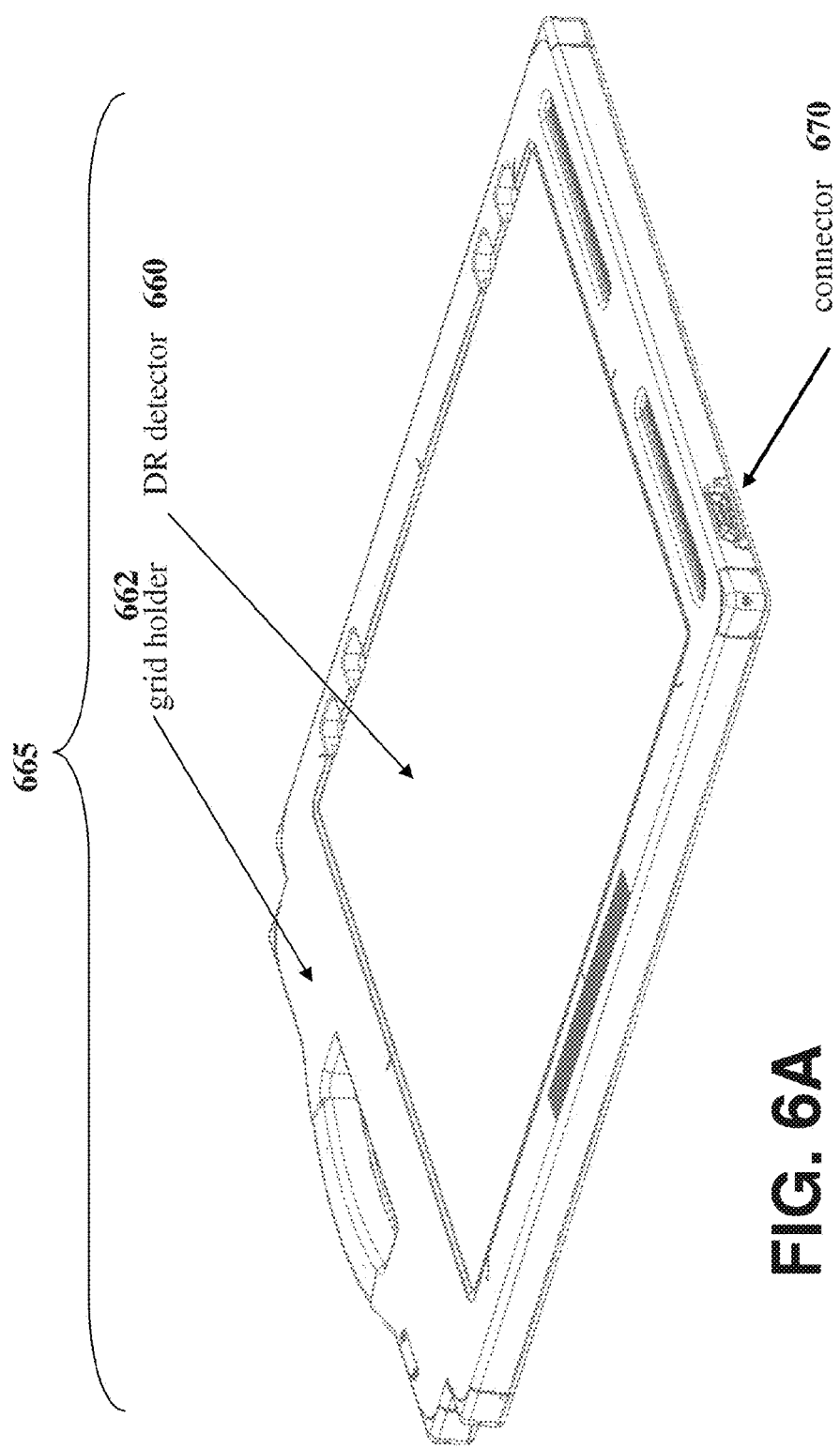

FIGS. 6A-6D are diagrams that illustrate an embodiment of a re-chargeable grid holder assembly with detector including a first connector for charging at a mobile radiographic system. As shown in FIGS. 6A-6D, an exemplary embodiment of a grid holder assembly 665 can include a grid holder 662, a DR detector 660 and a first type electrical connector 670. In one embodiment, the first type electrical connector 670 can be a female type connector, however embodiments herein are not intended to be so limited. The first type electrical connector 670 can be accessible at the grid holder 662, for example, by being exposed when mounted or integrally formed in an outer surface (e.g., side wall, upper surface) of the grid holder 662. The first type electrical connector 670 can include at least one recessed connection or engagable portion 672 and at least one connector alignment portion 674. As shown in FIG. 6D, the first type electrical connector 670 includes a plurality of 5 recessed engagable portions 672a, 672b, 672c, 672d, 672e and a plurality of 2 first alignment portions 674a and 674b. Although a single first type electrical connector 670 is shown in FIGS. 6A-6D, a plurality of connectors 670 can be used and can be accessible at various prescribed locations (e.g., opposite medial sides or corners, all four corresponding sides (left, right, front, back) etc.) on the grid holder 662 or at prescribed location(s) on the detector 660.

Figure 7A:
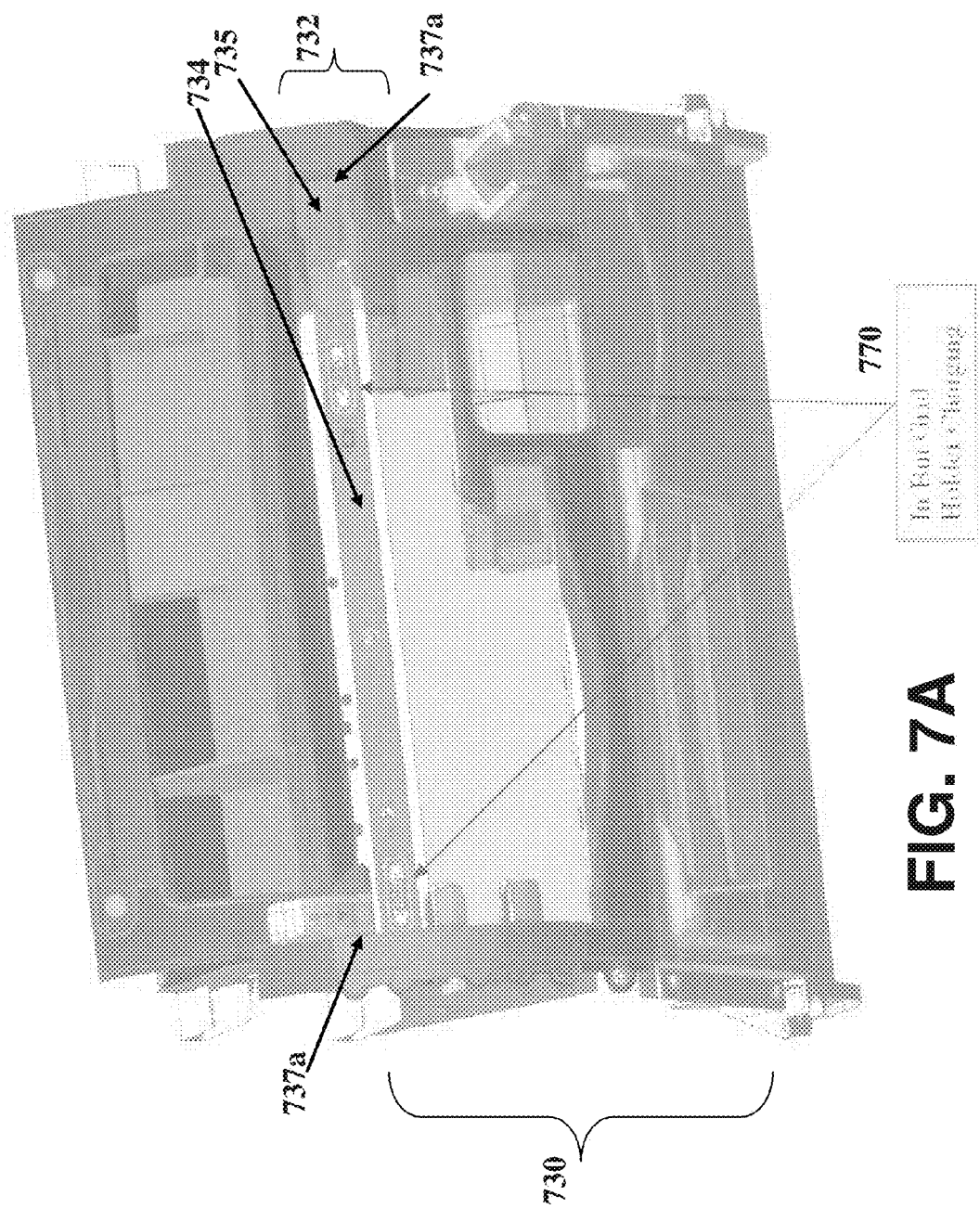
FIG. 7A is a diagram that illustrates a perspective view of an embodiment of an in-bin grid holder charging device including two connectors for mobile radiographic system according to the application.

FIGS. 7A-7C are diagrams that illustrate perspective, top and side views of an embodiment of a charging device including at least one connector accessible in the storage area for portable detectors in a mobile radiographic system. As shown in FIGS. 7A-7C, an exemplary embodiment of a recharge assembly on the moveable transport frame 420 can include a portion of storage area 730 and at least one second type electrical connector 770. In one embodiment, the second type electrical connector 770 can be a male type connector, however embodiments herein are not intended to be so limited. In one embodiment, the first connector and the second connector (e.g., 670, 770) are configured to align to each other and self-engage within a prescribed distance. The second type electrical connector 770 can be accessible at the storage area 730, for example, by being exposed when mounted in or integrally formed in an outer surface (e.g., bottom surface, side wall, side surface) of a recess or slot (e.g., storage 432, 434, 436, 438) in the storage area 730. The second type electrical connector 770 can include at least one protruded connection or engaging portion 772 and at least one connector alignment portion 774. As shown in FIGS. 7B-7C, the second type electrical connector 770 can include a plurality of 5 protruding engaging portions 772a, 772b, 772c, 772d, 772e and a plurality of 2 second alignment portions 774a and 774b. In one embodiment, the first alignment portions 674a and 674b and second alignment portions 774a and 774b can be correspondingly arranged magnets so that a first pole (e.g., north pole) of the first alignment portions 674a and 674b is attracted by a second pole (e.g., south pole) of the second alignment portions 774a and 774b. Although two second type electrical connectors 770 are shown in FIG. 7A, more or less connectors 770 can be used and can be accessible at various prescribed locations (e.g., opposite medial sides, center middle of bottom surface, plural corresponding sides (left, right, front, back) etc.) in a storage bin or large detector and grid storage 732 at the storage area 730.

In certain exemplary embodiments, positions of the first type electrical connector 670 on the grid holder 662 and the second type electrical connector 770 in the large detector and grid storage 732 are arranged to physically and/or electrically couple when the grid holder 662 is stored in the grid storage 732. For example, the first type electrical connector 670 can engage the second type electrical connector 770 when the first alignment portions 674a and 674b physically couple to the second alignment portions 774a and 774b, which can electrically couple the protruded connection portion 772 to the recessed connection portion 672.

Figure 8B:
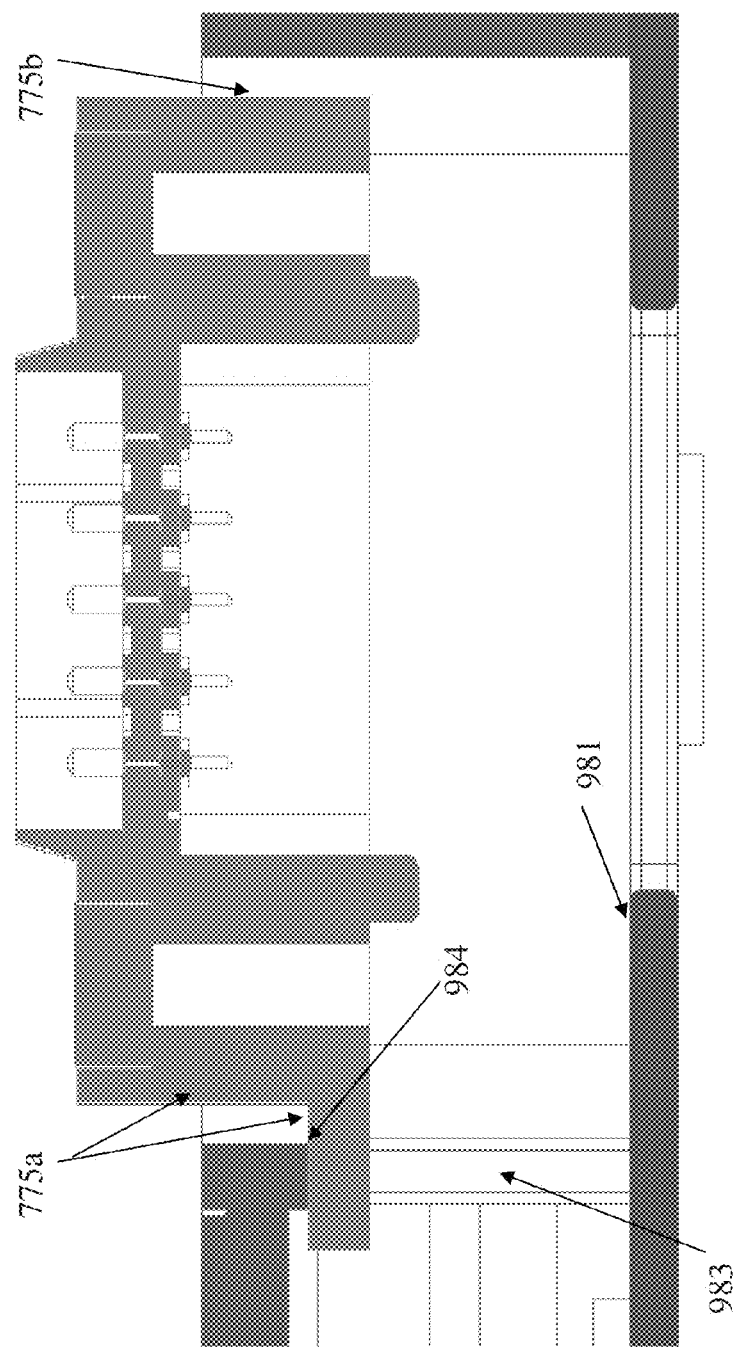
Figure 9A:
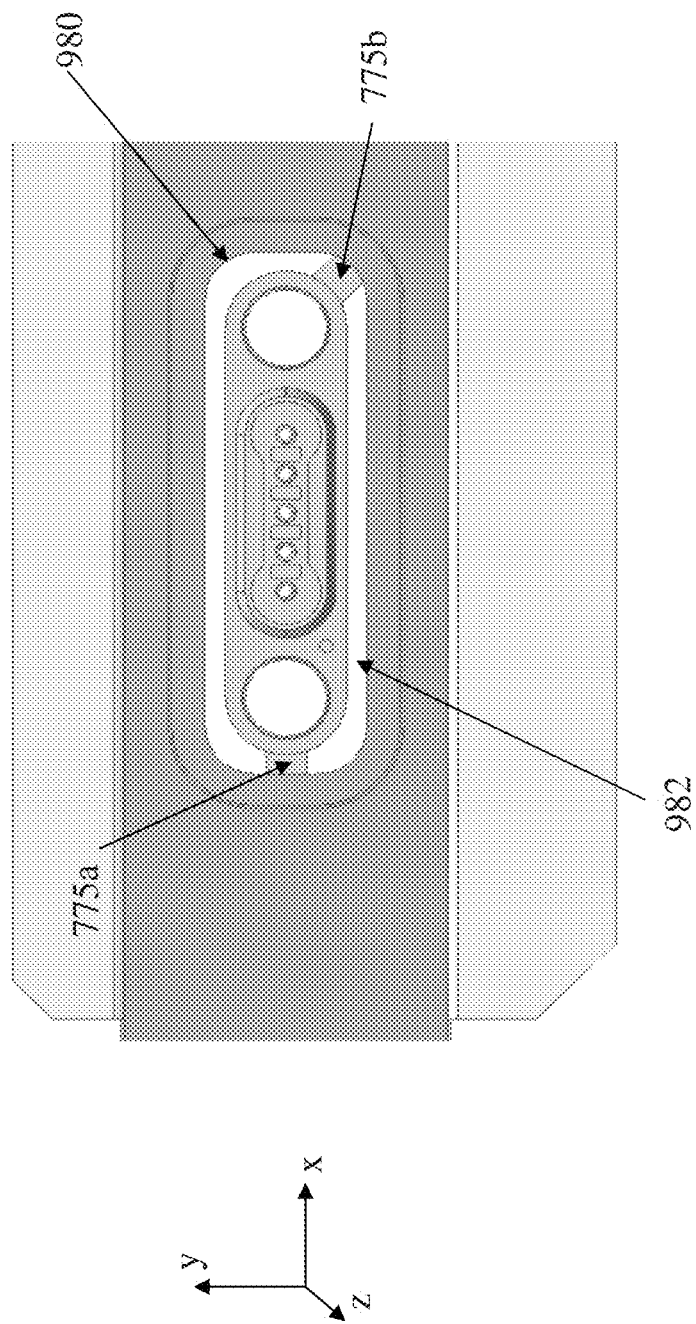
FIGS. 9A-9B are diagrams that illustrates top and bottom views of an embodiment of a connector for use at (e.g., a storage/charging slot) a mobile radiographic system according to the application.
Figure 9B:
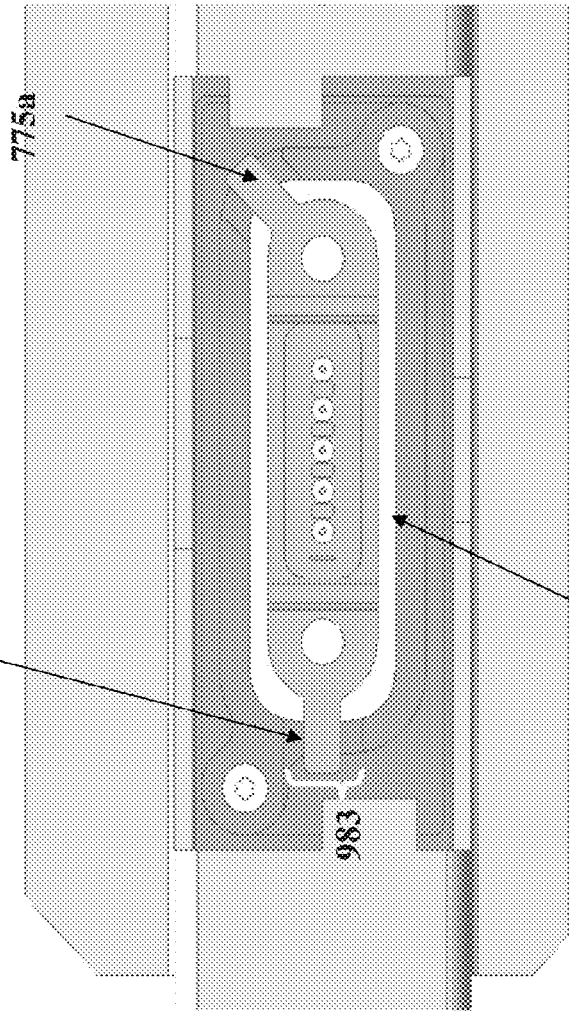

Embodiments of a charging device in a mobile radiographic system for portable detectors can include a connector system that can automatically mate (e.g., self-aligns, self-connects and self-disconnects) to a grid holder assembly or a portable DR detector and internal circuitry (not shown) can charge an on board battery (e.g., for the grid holder and/or a DR detector) when stored (e.g., in a storage area) at the mobile radiographic system. FIGS. 9A-9B are diagrams that illustrate top and bottom views of an embodiment of a connector accessible in the storage area for portable detectors in a mobile radiographic system. As shown in FIGS. 9A-9B, the second type electrical connector 770 can be restrained in the storage area 732 with the capability of three-dimensional movement for connection to the first type electrical connector 670. The second type electrical connector 770 can optionally include a first orientation projection 775a and a second orientation projection 775b. In one embodiment, the second type electrical connector 770 can be oriented by a single projection (or recess) configured to functionally provide limited (e.g., fastened) 3D movement. In one embodiment, the second type electrical connector 770 can be mounted in a recess 980 in a bottom surface of the storage area 732 that can be larger than the connector 770 in each of an x-direction, a y-direction and a z-direction, which can provide a gap (e.g., an air gap) in each direction. As shown in FIGS. 8A-8B, the first orientation projection 775a can limit movement of the second type electrical connector 770 in at least a z-direction within the recess 980 and the second orientation projection 775b can limit movement primarily in both the x-direction and the y-direction in the recess 980. In one embodiment, the second orientation projection 775b extends in both the x-direction and the y-direction from a body of the connector 770 a distance that is greater than the air gap 982 in both those directions. In one embodiment, the air gap is substantially the same in the x, y, and z directions. In another embodiment, the air gap is substantially different in one or more of the x, y, and z directions. The first orientation projection 775a can include a projection 775a1 that moves in a z-direction within a groove 983 between a bottom surface 981 of the recess 980 and a restraining upper surface 984 of the groove 983.

In one embodiment, the first orientation projection 775a (or second orientation projection) can be held within a connector housing (e.g., by restraining upper surface 984) to detach the second type electrical connector 770 from the grid holder assembly 665 (e.g., first type electrical connector 670) when the technician removes the grid holder assembly 665 from the storage slot 732. Alternatively, both the first and second orientation projections 775a, 775b can hold the second type electrical connector 770 within the recess 980 when the grid holder assembly 665 is removed from the storage slot 732.

Although the embodiment of FIGS. 8A-9C shows two orientation projections for the second type electrical connector 770 for controlled 3D movement when mounted in the storage area 732 (e.g., recess 980), the exemplary embodiments are not intended to be so limited. For example, a single orientation projection can be used to constrain motion in all of the x, y and z directions or one or more projections can be used to control the movement in each of the x, y or z-directions. In one embodiment, the projections can extend from surface of the recess 980 to contact corresponding surfaces, grooves or recesses in the second type electrical connector 770. Alternatively, the second type electrical connector 770 can be tethered by a cable to allow restrained controlled 3D movement in the storage slot 732. The second type electrical connector 770 can be restrained to limit motion to less than 5% of the dimensions of the storage area 732 or 0.1 to over 2 inches in respective directions. Preferable the second type electrical connector 770 is controlled for primary movement in the z-direction so that the movement in the z-direction can be 2×, 5× or 10× the movement in one of the x or y-directions.

In one embodiment, the second type electrical connector 770 can be rigidly mounted in the storage slot 732 (e.g., a bottom surface or side surface). In this embodiment, the grid holder assembly 665 can be physically moved until the first type electrical connector 670 is engaged to the second type electrical connector 770 (e.g., indicated to the technician by an audible or visual indicator).

In one embodiment, a mount (or storage slot 732 and second type electrical connector 770) can be implemented in mechanical or electro-mechanical combinations of elements. In contrast to a charging a radiographic detector in a recess, a mount embodiment can hold at least one radiographic detector, (power source thereof or detector carrier) in a charging position where the mount extends above a surface of the mobile radiographic apparatus (e.g., exterior surface of the transport frame). A detector charge device including a mount can provide the functionality to charge at least one portable radiographic detector at the mobile radiography apparatus. In one embodiment, a mount for a charging device at the mobile radiography system can include a magnetic tether connector, elastically oriented tethered connector, springs, pneumatic actuators or electro-mechanical actuators to make an electrical connection, female/male connector pairing using the at least one engaging connector, two physically corresponding electrical connectors. Such a mount can include but not be limited to one or more of a physical support for the detector, an alignment portion and an installation portion. In one embodiment, the alignment portion and/or the installation portion can be mechanical or electro-mechanical combinations of elements. In one embodiment, the mount can include a guide assembly and an electrical coupling portion. In one embodiment, the guide assembly and/or a coupling portion can be mechanical or electro-mechanical combinations of elements. In one embodiment, the mount can include actuator configured to move between a first position and a second position, where at least one engaging connector is configured to engage to charge a portable radiographic detector when the actuator is in the second position. In one embodiment, detector charge device can include a radiographic detector installer or adaptor that can include a mount or a recess configured to charge a first power source for the at least one portable radiographic detector at the mobile radiography apparatus. The mount or recess can include a detachable connector to releasable supply power to the at least one portable radiographic detector at the mobile radiography apparatus.

In one embodiment, the storage slot 732 is sized or configured to store the grid holder assembly 665. The storage slot can be angled or vertical relative to a base of the mobile radiographic imaging system. The technician can grasp the grid holder assembly 665 or an optional handle 667 thereof and insert a front end 666 (e.g., opposite the handle 667) into an open end of the storage slot 732. The front end 666 can include at least one first type electrical connector 670. Preferably, the technician can move the grid holder assembly 665 from a first position (e.g., in use; see FIG. 4A) outside the storage slot 732 to a second position where the grid holder assembly 665 is stored in the storage slot 732. In the stored second position, the first type electrical connector 670 can engage the second type electrical connector 770 (e.g., in a bottom surface 734). In the stored second position, the grid holder assembly 665 can rest against at least a bottom surface 734 of the storage slot 732. On route to the second position, the second type electrical connector 770 can move out toward a fully extended position while remaining at least partially within the recess 980 to engage the first type electrical connector 670. Since the second type electrical connector 770 has a range of motion between a fully retracted position (FIG. 8C) and a fully extended position (FIG. 8B), the engagement between the first and second type electrical connectors 670, 770 can be highly likely or assured in the second position of the grid holder assembly 665 even though a physical alignment between the grid holder assembly 665 can vary within the storage slot 732 in the second position.

In one embodiment, the second type electrical connector 770 can be implemented without a housing (e.g., movably attached/anchored to a surface of the transport frame). In one embodiment, the first type electrical connectors (e.g., connectors 670) can be implemented with limited movement in 2D or 3D and the second type electrical connectors (e.g., connectors 770) can be fixed or remain capable of limited movement.

In one embodiment, at least one interior surface of the storage slot 732 is configured to guide the first type electrical connector 670 toward the second type electrical connector 770 as the grid holder assembly 665 is moved into the storage slot 732. For example, the storage slot 732 can have a decreasing cross-sectional size to guide the grid holder assembly 665 to the second position (e.g., FIGS. 14A, 14B). Accordingly, as shown in FIG. 7A, a guide portion 735 in at least one interior surface of the storage slot 732 can guide the grid holder assembly 665 to the second position to make a physical location of the second position of the grid holder assembly 665 in the storage slot 732 more repeatable.

In one embodiment, at least one side surface of the storage slot 732 can include the guide portion 735 (e.g., projected lengthwise along at least a portion of the storage slot 732) that extends into the storage slot 732 as the guide portion 735 is closer to the bottom surface 734 of the storage slot 732. Alternatively, both opposite side surfaces 737a and 737b (e.g., three surfaces or all interior surfaces) can include guide portions to make a physical location of the second position of the grid holder assembly 665 in the storage slot 732 more repeatable.

In one embodiment, resistance or force against the grid holder assembly 665 can increase as the grid holder assembly 665 moves from an opening toward the bottom surface 734 (e.g., the second position) of the storage slot 732. In one embodiment, the resistance against the grid holder assembly 6656 that increases can be provided by the guide portion 735. Since the weight of the DR detector 660, the grid holder 662 or the grid holder assembly 665 are each significant, embodiments of the storage slot can reduce or prevent damage to these parts by reducing or preventing shock or impact damage from placing these parts into the storage slot 732 (e.g., striking the bottom surface 734). For example, the storage slot can use friction as a resistance. Thus, in one embodiment, the storage slot 732 can have a decreasing cross-sectional size to use friction between opposing sides of the storage slot and sides of the grid holder assembly to reduce a speed of the grid holder assembly 665 into the storage slot 732 (e.g., the second position, FIGS. 14A-14B). In one embodiment, the increase resistance can be provided by elastic member(s) (e.g., springs, etc.) that can apply force through the guide portion 735, through surfaces of the storage area or directly to surfaces of the grid holder assembly 665 or detector to be stored.

Figure 10:
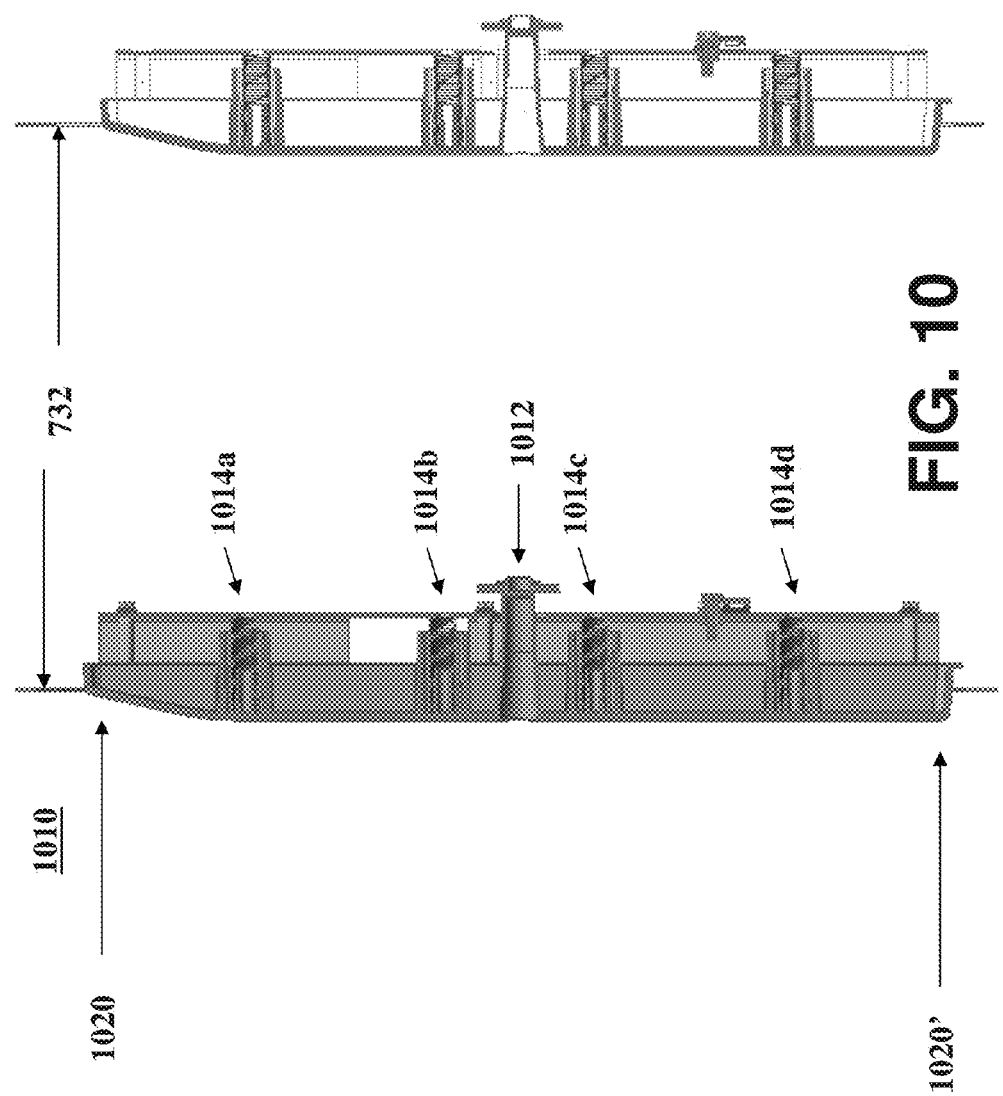
FIG. 10 is a diagram that illustrates an embodiment of a guide assembly for use in storage/charging slot at a mobile radiographic system according to the application.

FIG. 10 is a diagram that illustrates an embodiment of a guide bar (e.g., pressure plate assembly) for use in a storage/charging slot at a mobile radiographic system. In one embodiment, the storage slot 732 can include a vertically extending guide bar 1010 along at least one side edge to resist (e.g., elastically) the grid holder assembly 665 descending into or entering the storage slot 732. In FIG. 10, both a perspective view of an interior of the guide bar 1010 and a cross-sectional view of the guide bar 1010 is provided. The guide bar 1010 can be mounted to the storage slot 732 using anchor 1012 and spring loaded by elastic members or springs 1014a-1014d to push against at least one side of the grid holder assembly 665 to reduce a speed of the grid holder assembly 665 into the storage slot 732. As shown in FIG. 10, the guide bar 1010 can have a profile that extends away from a side of the storage slot 732 as the guide bar 1010 traverses from a top 1020 to a bottom 1020' of the guide bar 1010. In one embodiment, the friction or pressure can increase (e.g., linearly or non-linearly) as the grid holder assembly 665 travels closer to the charging position or bottom of the storage/charging slot. For example, the guide bar 1010 can provide sufficient force so that the technician can has to push slightly to get the grid holder assembly 665 to the second position (e.g., a charging position) or to the bottom surface 734 of the storage/charging slot 732.

In one embodiment, the storage/charging slot for charging the grid assembly holder can include a suspension mechanism or cushioning mechanism to reduce an impact to the grid holder assembly 665 when being moved to the second position or being moved to strike a bottom surface 734 of the storage slot 732. In one embodiment, a suspension mechanism can be part of or extend above the bottom surface 734 to elastically resist movement by the grid holder assembly 665 to reach or upon reaching the bottom surface 734. FIG. 8A is a diagram that illustrates an embodiment of a suspension bar (e.g., suspension assembly) for use in a storage slot at a mobile radiographic system. In FIG. 8A, both a perspective view of an interior of the suspension bar 810 and a cross-sectional view of the suspension bar 810 is provided. The suspension bar 810 can be mounted to the storage slot 732 using anchor 812 and spring loaded by elastic members or springs 814*a*-814*d* to push against at a corresponding side of the grid holder assembly 665 to reduce a speed or impact of the grid holder assembly 665 into the bottom surface 734. In one embodiment, the second type electrical connector 770 can be rigidly or movably (as shown in expanded view) mounted at, attached to or part of the suspension bar 810.

Figure 12B:
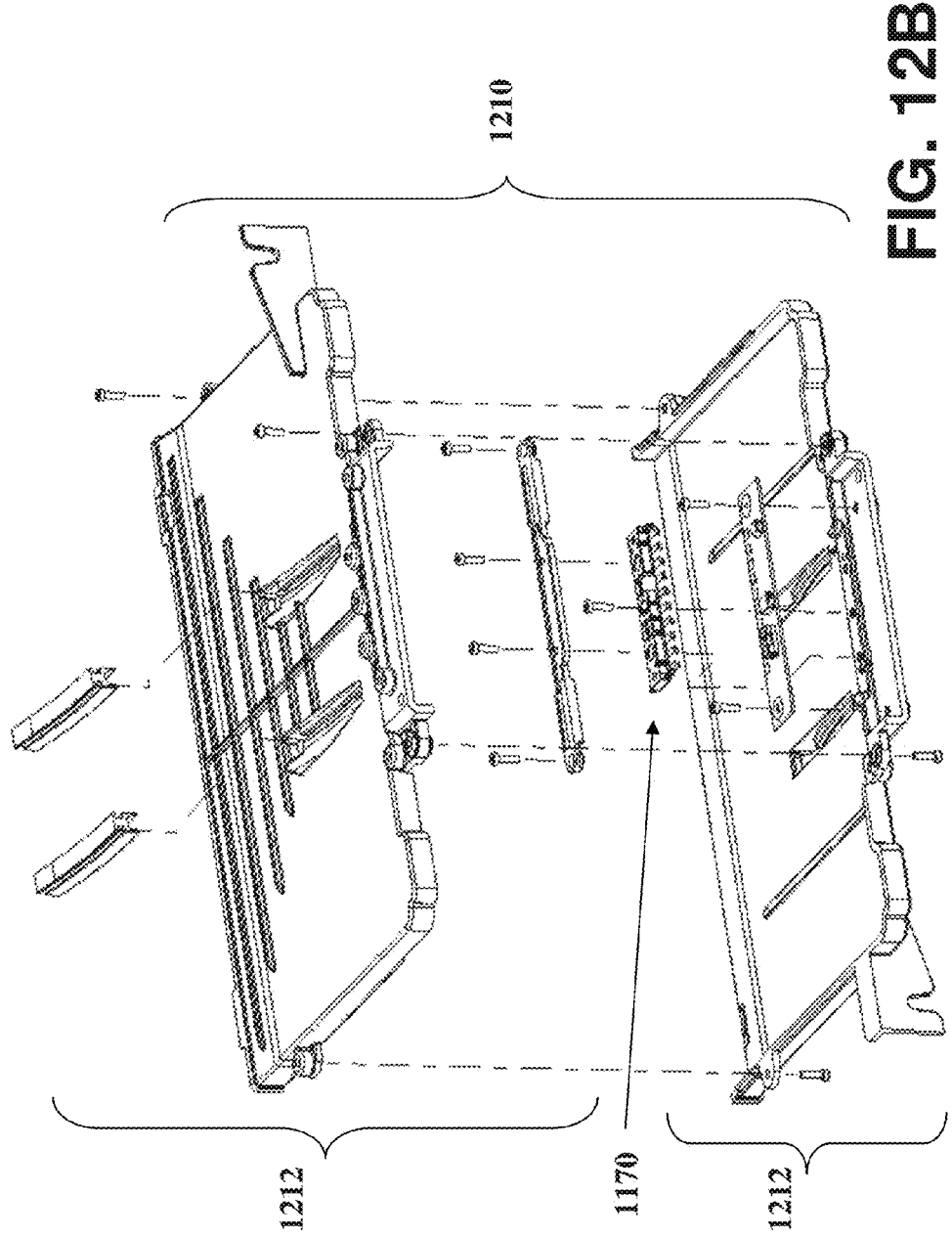
Figure 12C:
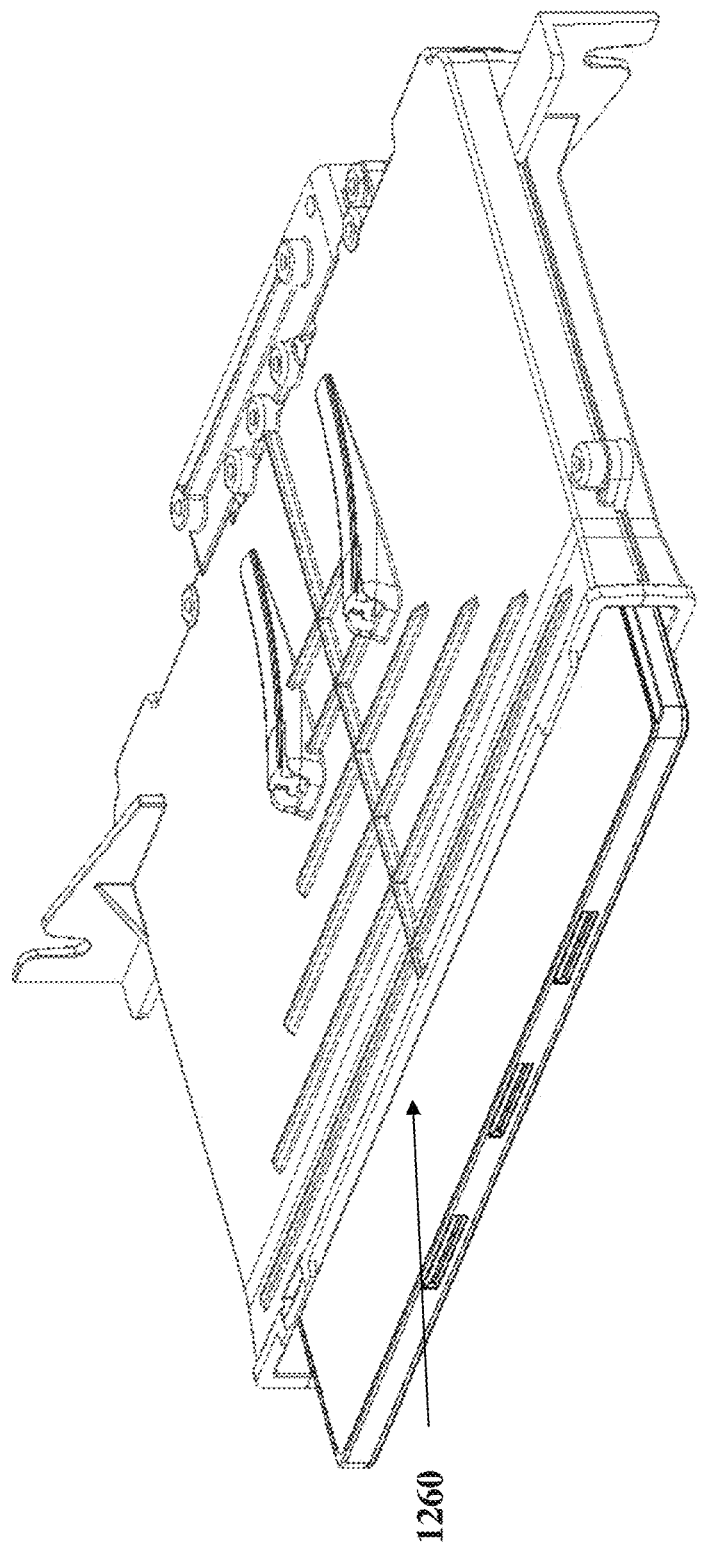
Figure 12D:
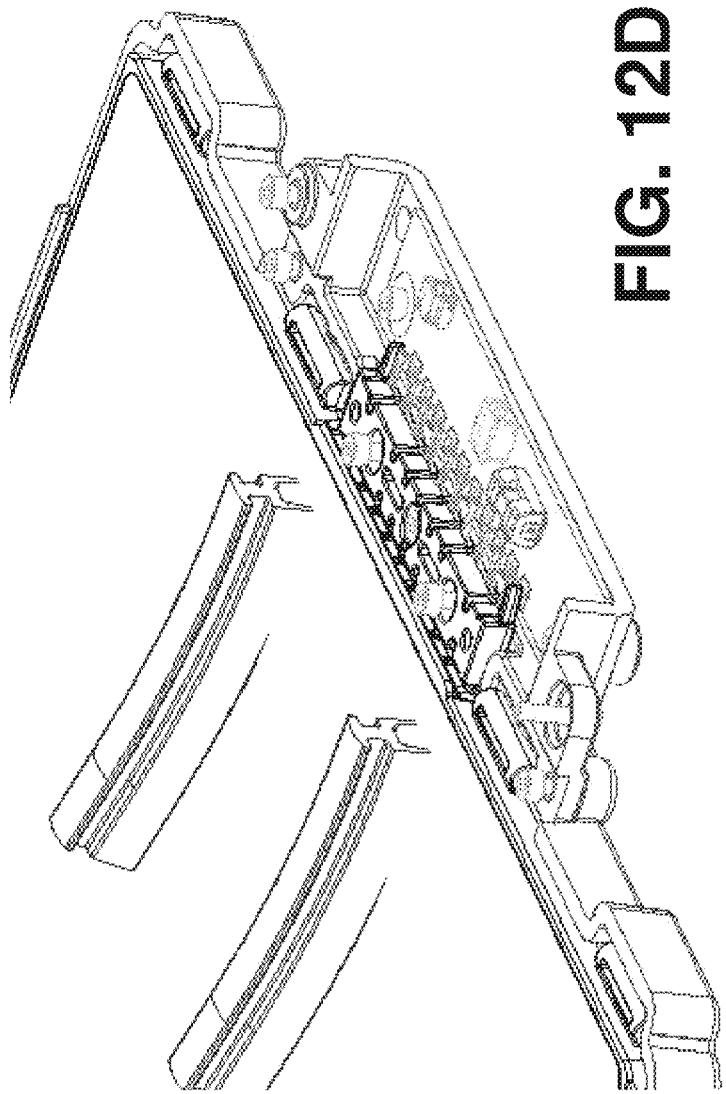
Figure 12E:
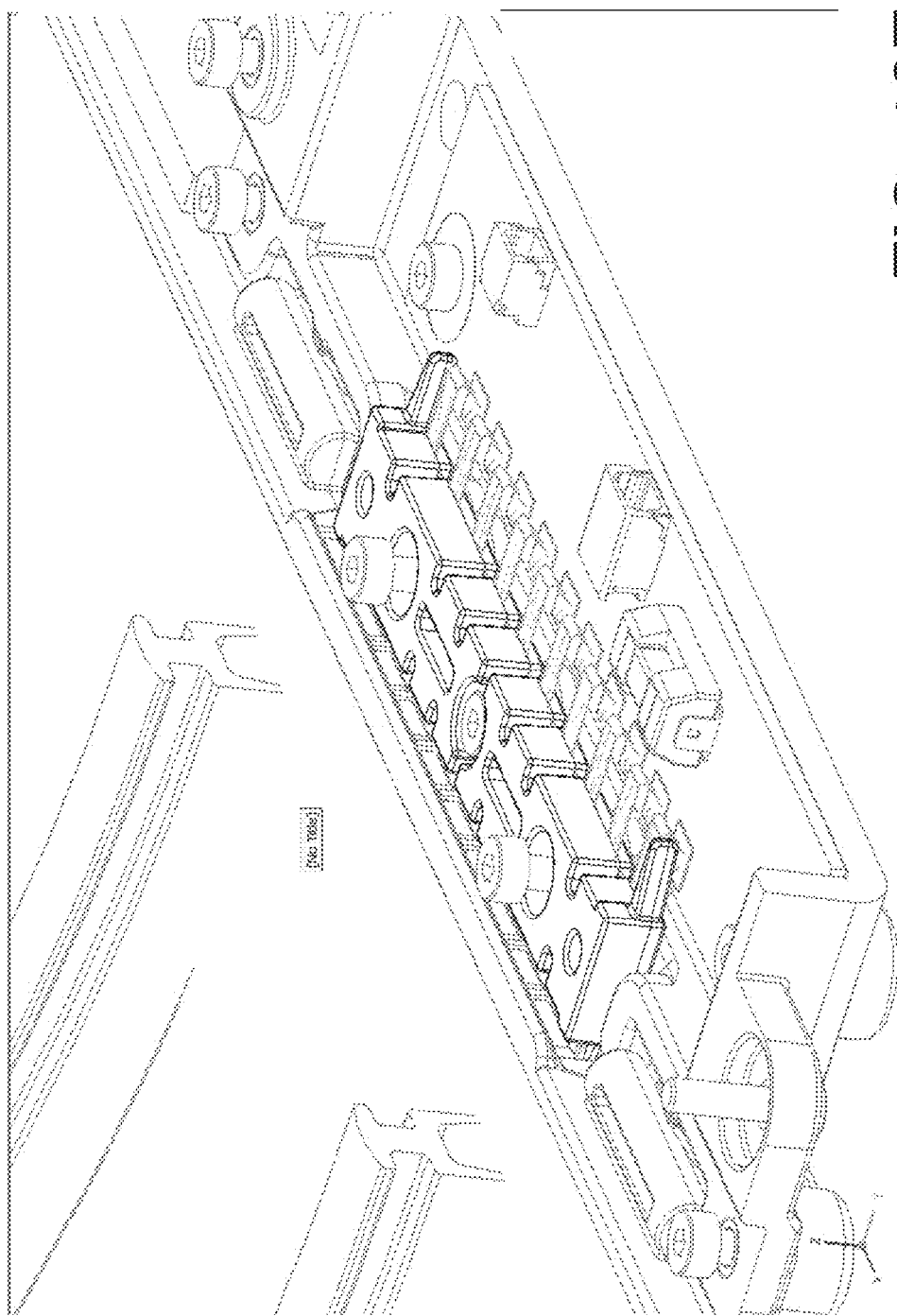
Figure 12F:
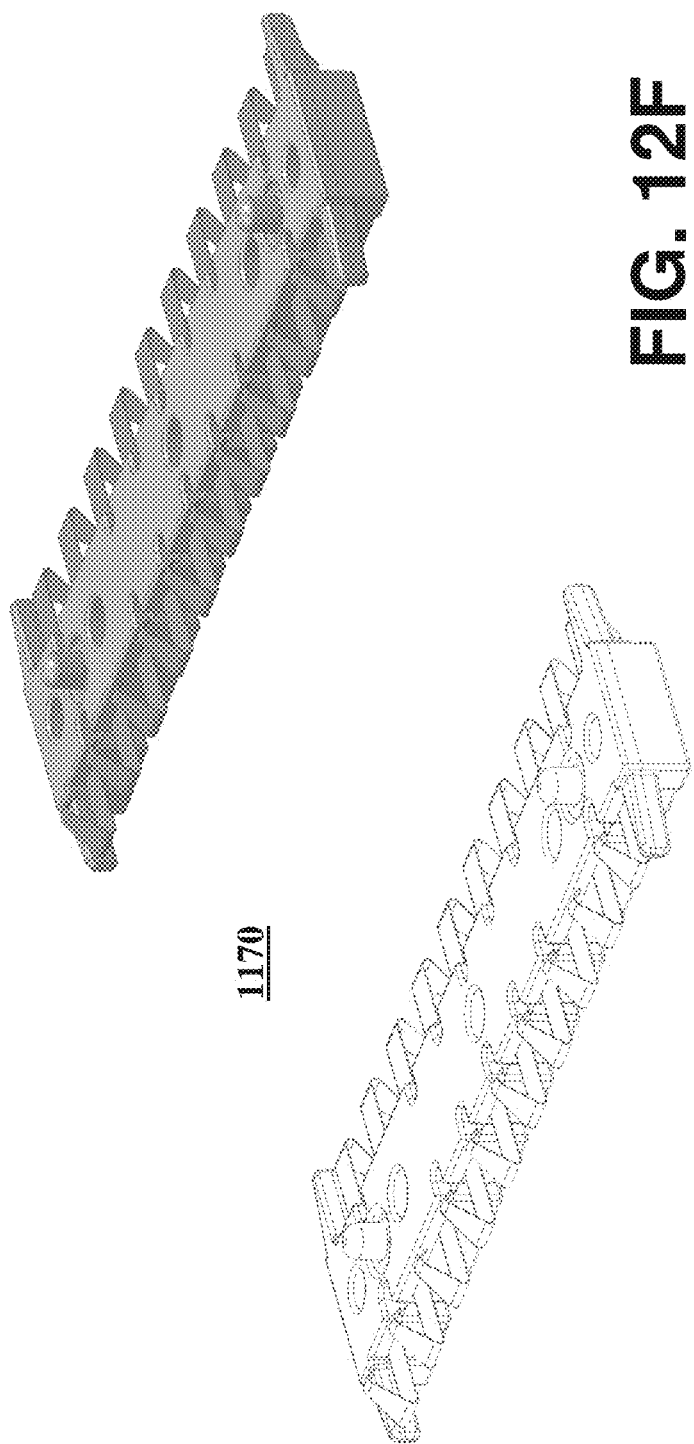

FIG. 11 is a diagram that illustrates a perspective view of an embodiment of a battery charging device in a storage area or bin including a connector for use at a mobile radiographic system. FIG. 12A-12F are diagrams that illustrate various views of an embodiment of an in bin battery charging device including a connector for use at a mobile radiographic system. As shown in FIGS. 11-12F, a charger housing assembly 1210 can include a housing assembly 1212 and a battery charger connector 1170. For example, the charger housing assembly 1210 can be mounted in a storage area 730 of the mobile radiographic system to charge a battery removed from a detector 660 (or grid holder, etc.) when the battery is mounted in the charger housing assembly 1210 in a storage slot such as storage slot 738. FIGS. 12A and 12C illustrate a power source 1260 (e.g., battery) mounted in the charger housing assembly 1210.

Accordingly, exemplary mobile radiographic apparatus including embodiments of charging devices can provide at least two charging capabilities for portable detectors, batteries therefore or grid holders to increase availability of portable detectors for imaging applications.

Embodiments of a charge apparatus, charging methods and/or mobile radiographic imaging systems can include one or more indicators (e.g., audible or visual) that can alert personnel when the grid holder assembly 665 (or detector 660 or battery 1260) reaches a charging position in the storage slot 732. In one embodiment, the charging position of the grid holder assembly 665 can be achieved by engagement of the first type electrical connector 670 to the second type electrical connector 770. In the charging position (e.g., second position), one or more power sources of the grid holder 662 and the detector 660 can be recharged.

Alert indicator 110 may be a discrete device, such as an audible alarm, a light emitter, or other element that generates an audible or visible signal, or a message or symbol that displays on a control monitor, for example. It should be noted that charge apparatus XX may be provided on mobile radiography apparatus 600, and use a logic processor and other components provided and built into the mobile radiographic system (e.g., transport frame 420).

The alert may be provided at the DR detector 660 itself, such as with a beeping sound generated at the DR detector 660. A visual indicator at DR detector 660 may also be used, separately or in conjunction with an audible indicator. In an alternate embodiment, the alert indication is provided at both the mobile radiographic imaging system (e.g., 400) and the detector 660 and/or grid holder 662. In another alternate embodiment, a display device that is part of detector 660, grid holder 662 or coupled thereto can provide visual information regarding a charging status.

Figure 13:
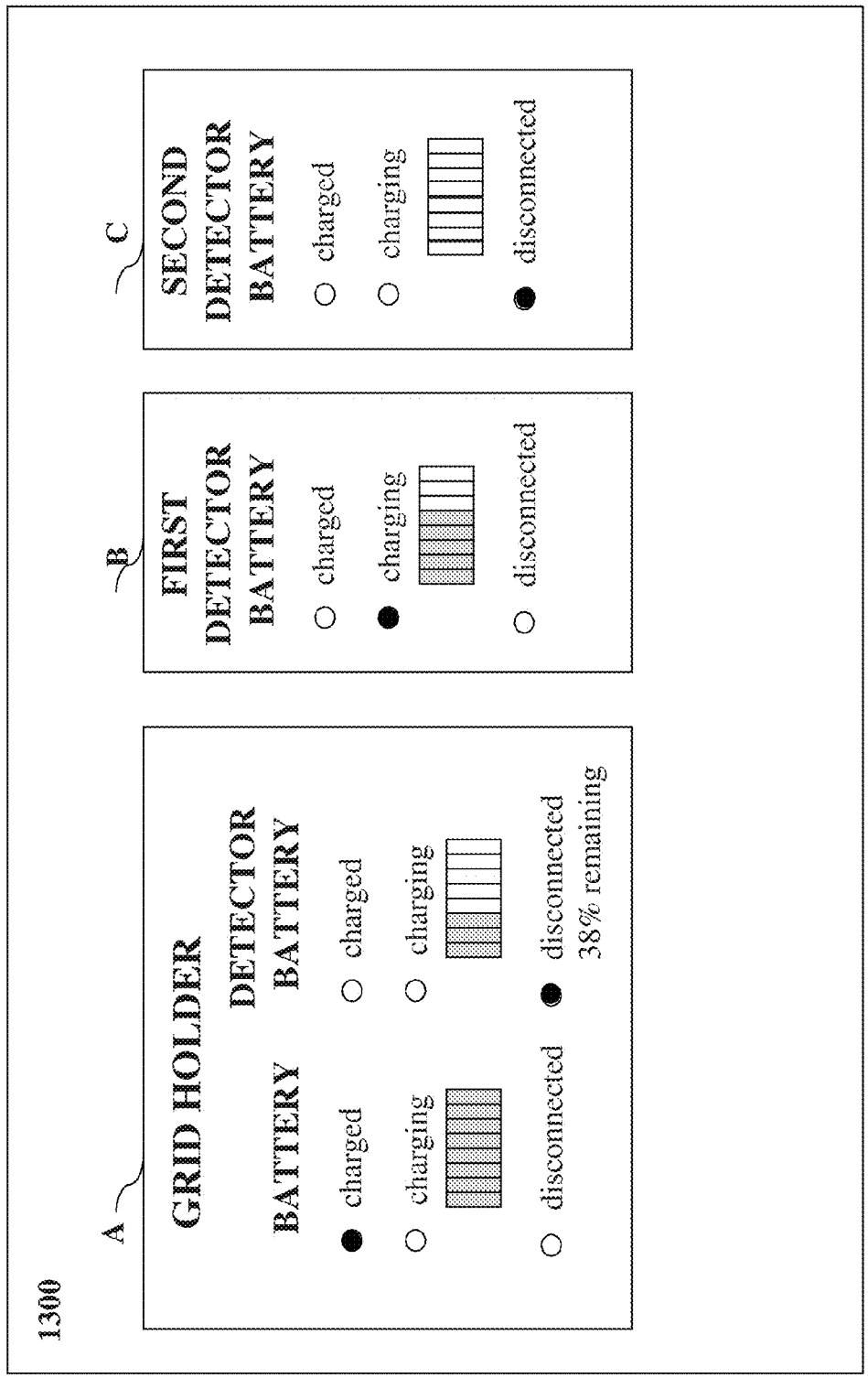
FIG. 13 is a diagram that shows an embodiment of a charging status viewable on a display at a mobile radiographic system according to the application.

FIG. 13 is a diagram that illustrates an embodiment of a charging status viewable on a display or operator console that may be located on at a mobile radiographic system. As shown in FIG. 13, an example charge status screen 1300 can include one or more status screens A, B, C that display status for the various storage slots of the storage area 730 or various rechargeable devices to be charged by the mobile radiographic system. For example, status screens A, B, C can illustrate whether a grid holder, detector or removed battery is connected (e.g., and a charge level thereof) or disconnected. Alternatively, a time until complete charge or the like can be displayed at the charge status screen 1300. In one embodiment, a touch screen interface can be used for the charge status screen 1300 to allow active remote control to reciprocally move between a connected/charging status and a disconnected status in the storage area or storage slot 732. In one embodiment, the indicators 110 can be displayed in the charge status screen 1300.

Figure 14B:
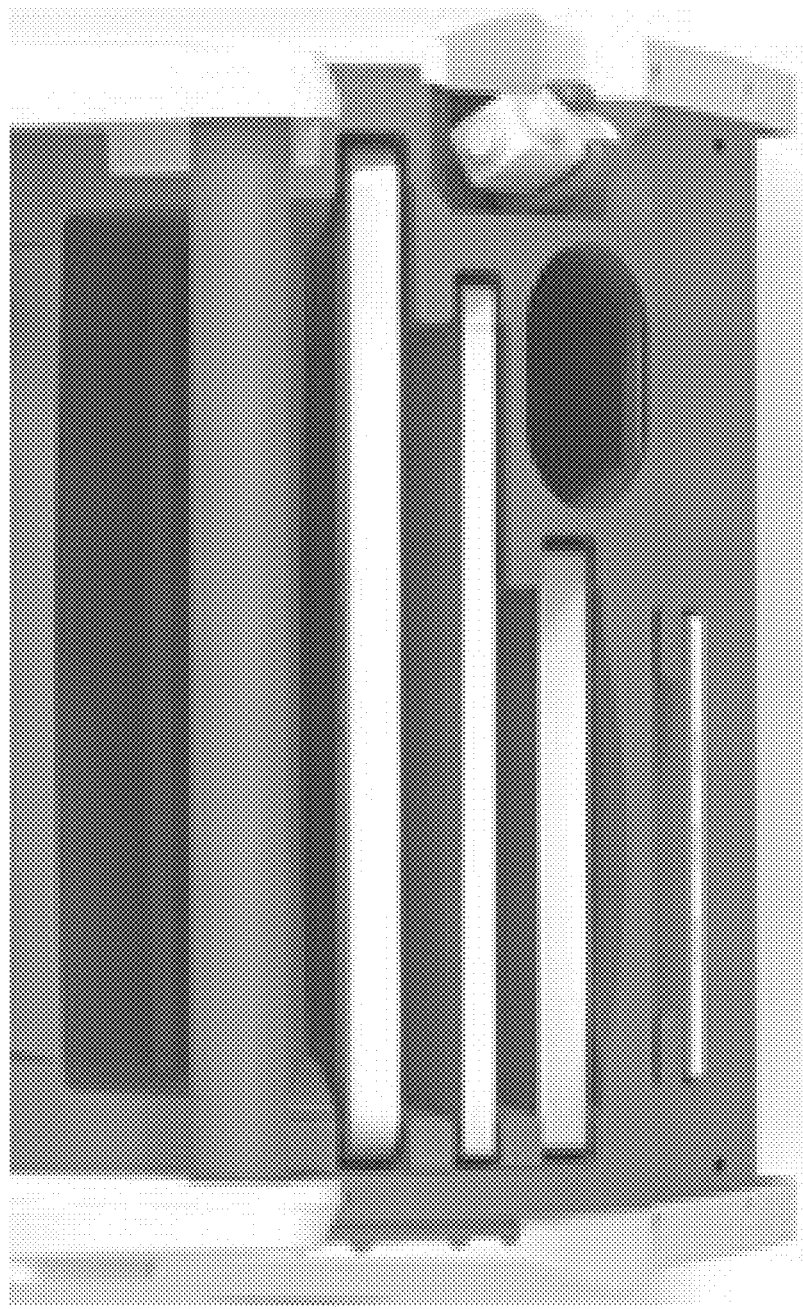

FIGS. 14A-14B are diagrams that show various views of an embodiment of a grid holder, detector, battery storage/charging area for a mobile radiography unit according to the application.

Figure 15:
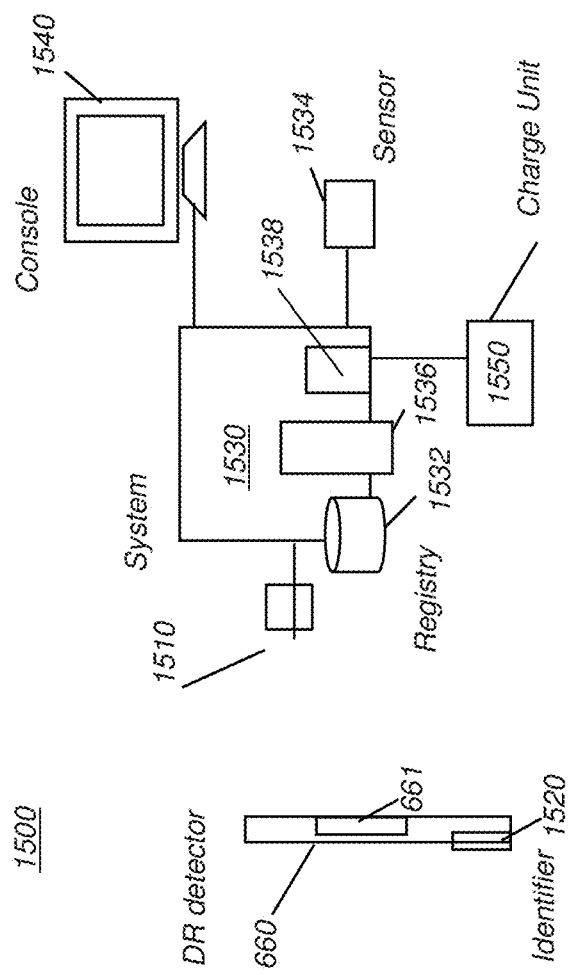
FIG. 15 is a diagram that shows an exemplary mobile radiography system charge system embodiment.

The schematic block diagram of FIG. 15 shows components of a charge system for management of detectors power level/charging status. As shown in FIG. 15, a charge system 1500 can manage the power level/charging status for a plurality of associated detectors (e.g., detectors 460, 660). An identifier 1520, described in more detail subsequently, provides a unique identifying mechanism for a particular detector 660. Identifier 1520 is used to link DR detector 660 to one or more x-ray systems 1530, which may be one or more stationary x-ray installations or one or more mobile radiography systems (e.g., systems 400, 600) that travel throughout a site. System 1530 has an associated processor 1536, such as a computer or dedicated logic processor, that maintains a registry 1532 of one or more associated DR detectors 660. Registry 1532 can include a memory for storage of power level, linkage information and other status information about one or more DR detectors 660 and can associate selected detectors 660 with system 1530. In one embodiment, one or more associated DR detectors 660 can be mounted in a grid holder 662. The act of registering DR detector 660 to system 1530 in registry 1532 may be performed by operator entry at a control console 1540 or by an automatic or semi-automatic method using an optional registration sensor 1534. According to one embodiment, registration sensor 1534 and identifier 1520 can both be near field communications (NFC) RF device or other two-way communications device that communicates with each other when in close proximity.

Registration is not solely for power status monitoring, but typically has other purposes, such as to validate data only from appropriate DR detectors 660, to help reduce or prevent confusion so that only data from a registered DR detector 660 is transferred to system 1530. System 1530 can have multiple DR detectors 660 registered, according to one embodiment, but can be set up to communicate only with one designated DR detector at a time. Thus, a library of available DR detectors 660 can be maintained at system 1530 so that one or another detector can be designated for a particular imaging situation. System 1530 can maintain power level information, calibration files or other information for a number of DR detectors 660 in an active listing, from which the designated DR detector for a particular exam can be selected. De-registration can be used to make a particular DR detector 660 inactive or not associated with a particular system.

Charge system 1500 includes one or more indicators 1510 that alert personnel to a charging status and/or charge status change for DR detectors 660 assigned to the system. Alert indicator 1510 may be a discrete device, such as an audible alarm, a light emitter, or other element that generates an audible or visible signal, or a message or symbol that displays on a control monitor, for example. It should be noted that charge system 1500 may be provided on mobile radiography apparatus 400, using a logic processor and other components provided and built into transport frame 420, or may be resident in processor at a location that is associated with a stationary x-ray system site. The alert may be provided at the target x-ray system 1530 or at the DR detector 660 itself, such as with a audible and/or visual indication generated at the DR detector 660. In an alternate embodiment, the alert indication is provided at both the system 1530 and the detector 660. In another alternate embodiment, a display device that is part of detector 660 or coupled to detector 660 can provide text or symbolic information that indicates connection to charge device, removal from charge device, charging status and the like (e.g., see FIG. 13). The use of DR detector 660 power status information can be particularly useful in a wireless environment, so that data associated with a particular detector 660 is properly acknowledged, identified, and transferred from DR detector 660.

System 1500 can include a first power source 1538 and a charge unit 1550. The charge unit 1550 can charge a power source for multiple DR detectors 660 at one time by selective connection to the first power source 1538. The charge unit 1550 can include one or more first type charge connectors to connect to a DR detector 660, one or more second type charge connectors to connect to a detector power source (e.g., battery) removed from the detector and/or one or more third type charge connectors to connect to a detector carrier (e.g., grid holder). In the use of the first and third type charge connectors, the first power source 1538 is electrically coupled (e.g., directly/through a connector on the DR detector and internal circuitry of the DR detector to a power source 661 so that the power source 661 can be charged (without being removed from the detector 660/grid holder 662).

In one embodiment, a charge system 1500 or system 1530 can include the power source 1538, the second type connector 770 and the storage area 732. In one embodiment, the charge system 1500 can include a mount or recess to provide support or attachment at mobile radiography system (e.g., transport frame 420) to a detector to be charged. In one embodiment, a power status of charging or associated DR detectors (e.g., reported wirelessly or through system 1530 or charge unit 1550), can be displayed on the display 1540.

Figure 16:
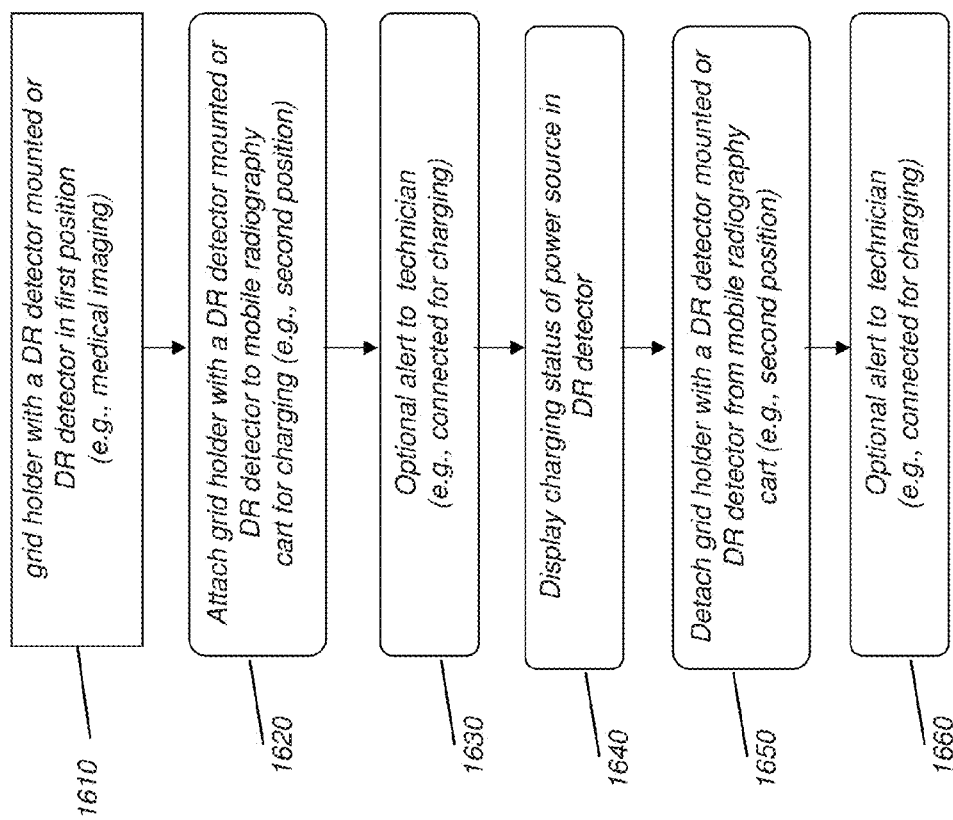
FIG. 16 is a flow chart that shows an exemplary method embodiment of charging a portable radiographic detector at a mobile x-ray cart.

Referring to FIG. 16, a flow chart that shows an exemplary method embodiment of charging a portable radiographic detector at a mobile x-ray cart according to the application will now be described. A method embodiment for charging a portable radiographic detector at a mobile x-ray cart will be described using embodiments of charge apparatus shown in FIGS. 6A-15 and can be applied or retrofit to mobile x-ray systems/carts shown in FIGS. 1-5B; however, the method of FIG. 16 is not intended to be limited thereby.

Figure 6B:
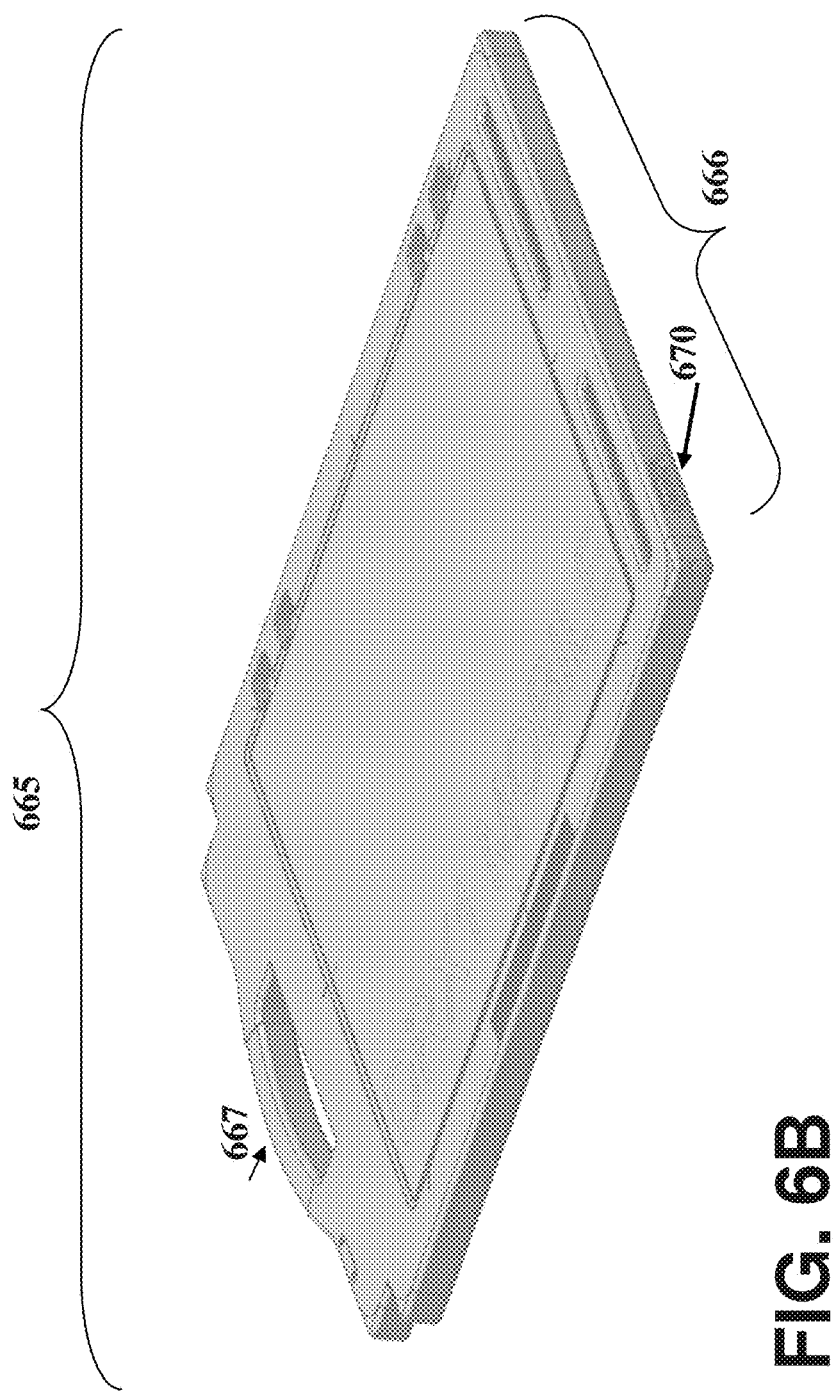

As shown in FIGS. 6A-6B, a DR detector 660 can be mounted in a grid holder 662. The grid holder 662 can include a handle 667 and a first type connector 670. The technician can hold the grid holder 662 with a DR detector 660 snapped-in by the handle 667 in a first position detached (e.g., FIGS. 5A, 6A) from a mobile x-ray cart (e.g., mobile x-ray cart 1400) (operation block 1610). Then, the technician can move (e.g., install or charge) the grid holder 662 with a DR detector 660 snapped-in to the mobile x-ray cart 1400 into a second charging position where a power source of the mobile x-ray cart is electrically coupled to a power source in the DR detector 660 snapped-in at the grid holder 662 (operation block 1620). Optionally, an audible or visual alert can be provided to the technician when the second charging position is achieved (operation block 1630). In one embodiment, the technician can move a DR detector 660 itself from the first position detached from the mobile x-ray cart to the second charging position mounted at the mobile x-ray cart where a power source of the mobile x-ray cart is electrically coupled to a power source in the DR detector 660.

Then, while in the second charging position mounted at the mobile x-ray cart, a charging status can be displayed (operation block 1640). In one embodiment, a small display window at charge device can display a charge status (e.g., percent battery power). Alternatively, a charge status can be displayed at the transport frame or the detector itself. In another embodiment, a charging status (e.g., one or more battery/detector/grid holder charge status screens) can be provided on a display or operator console that may be located on at a mobile x-ray cart.

Then, the technician can remove or detach the grid holder 662 with a DR detector 660 snapped-in from second charging position (operation block 1650). In one embodiment, the technician can transfer the grid holder 662 with a DR detector 660 snapped-in from second charging position by removing the grid holder 662 with a DR detector 660 snapped-in from the mobile x-ray cart 1400 (e.g., to the first position). Optionally, an audible or visual alert can be provided to the technician when the second charging position is released (operation block 1660).

In certain exemplary embodiments, a charge system embodiment can be retrofit to an existing mobile radiography system. For example, the charge unit 1550 or the charge system 1500 (in whole or in part) can be implemented or retrofit into the mobile radiography system of FIG. 1. Alternatively, an electronic connection can be implemented to a single charging mount (or recess) or multiple types of charging mounts installed to an existing mobile radiography system. In one embodiment, an existing storage area can be replaced with a recess or storage area 732 including an engagable connector (e.g., second type connector 770) for connection to a power source of the existing mobile radiography system.

In one embodiment, an inductive charging mount can be incorporated into the charge unit 1550 or the charge system 1500. Inductive charging can use an electromagnetic field to transfer energy between two objects (e.g., using a charging station). For example, energy can sent through inductive coupling to an electrical device, which then can use that energy to charge a power source such as batteries. In one embodiment, a mobile radiography system can implement a charging mount or recess (e.g., at a transport frame 420) using an inductive charging apparatus to charge removed batteries or portable radiographic detectors. For example, an alternating electromagnetic field created in a mobile radiography cart charging system by an induction coil would be introduced to a second induction coil present in the grid holder, and the second induction coil would convert energy contained in the field into electrical current to charge a battery. In one embodiment, the inductive charge unit 1550' can securely charge a power source for a detector at a prescribed location at the mobile radiography system.

Figure 17A:
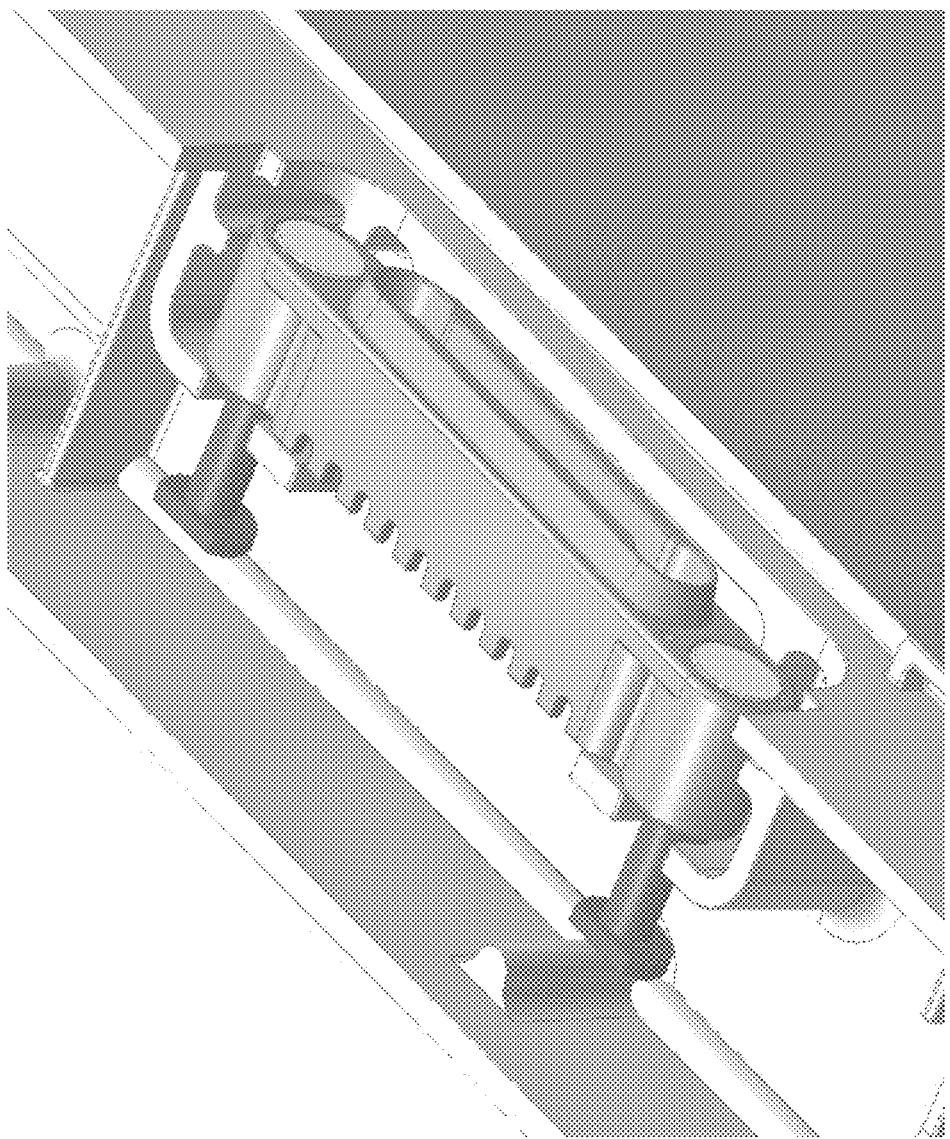
FIGS. 17A-17C are diagrams that show top and side views of an exemplary connector embodiment (e.g., for use at a mount or an in-bin grid holder or the like) charging device for mobile radiographic system according to the application.
Figure 17B:
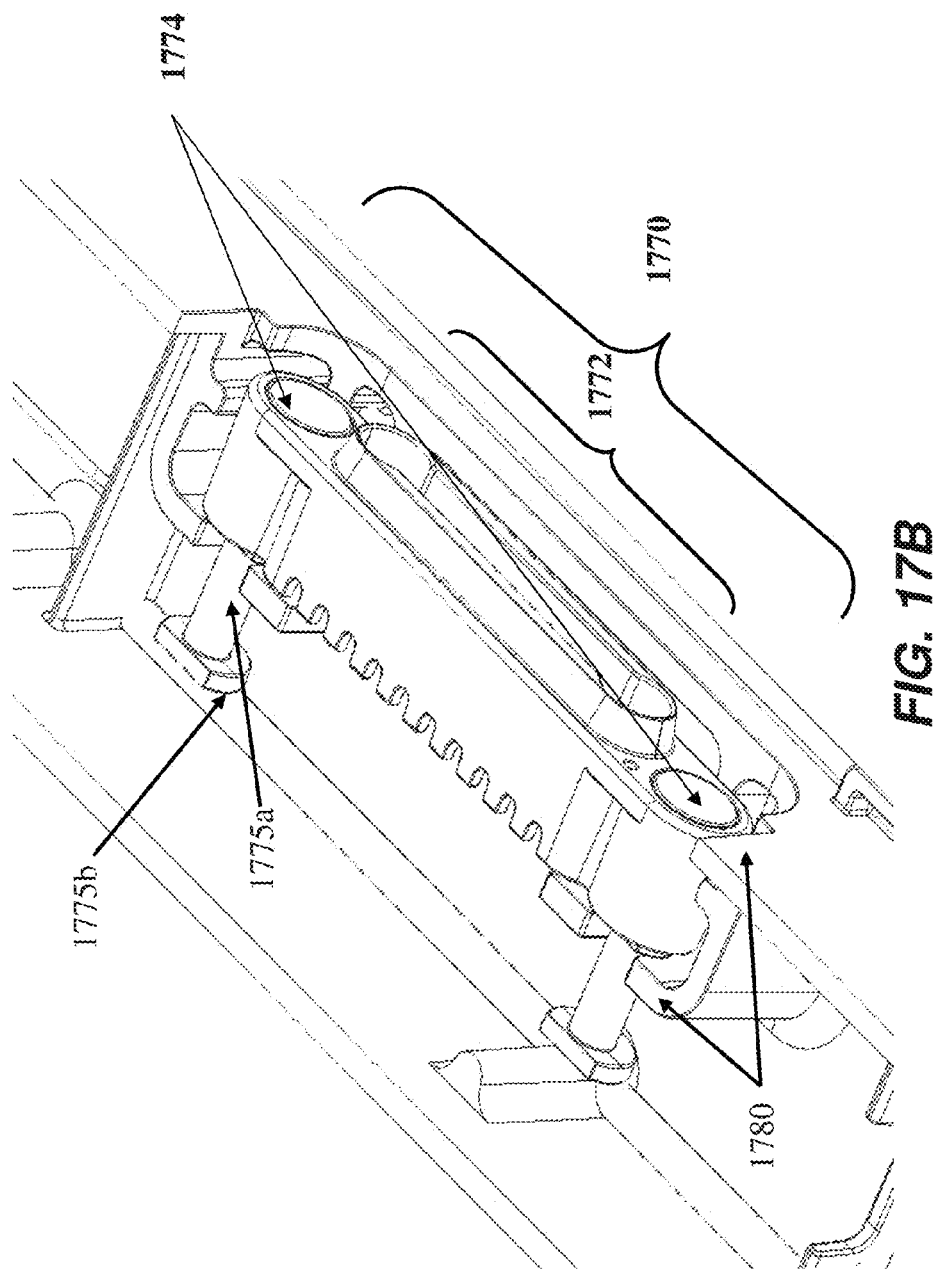
Figure 17C:
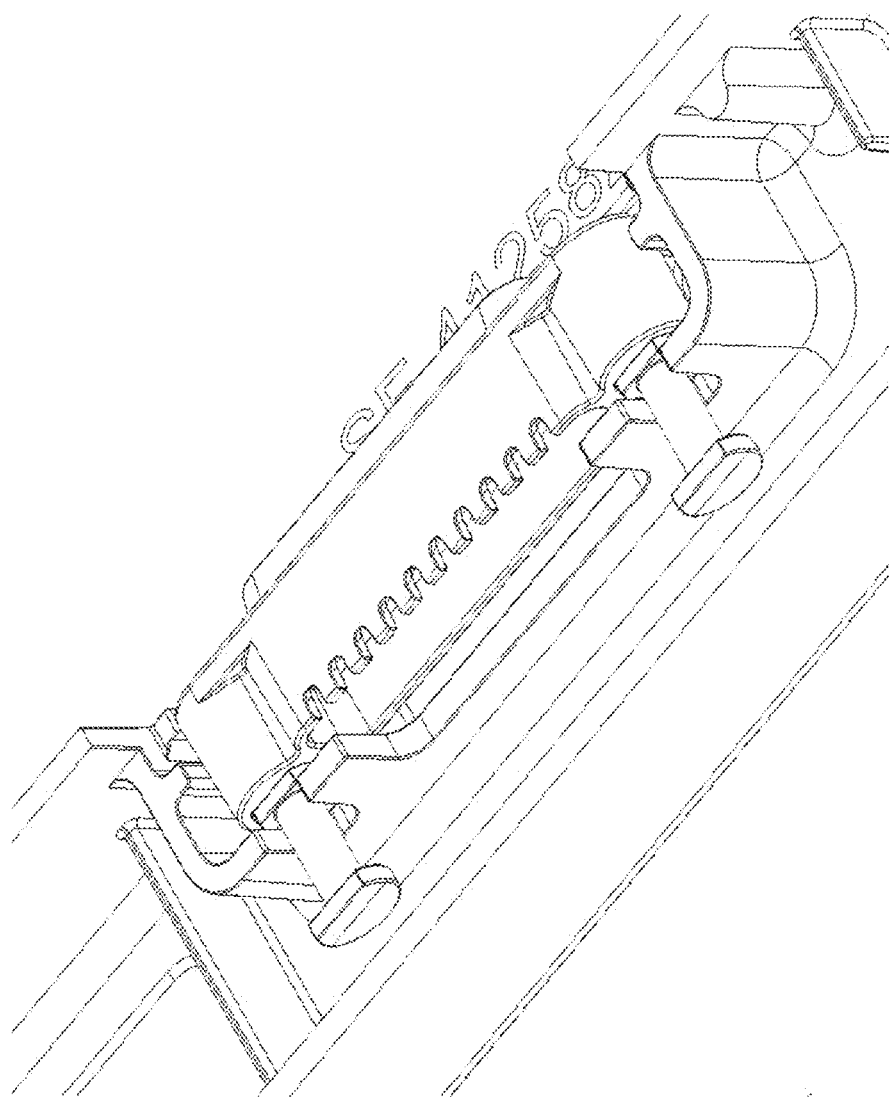

Embodiments of a charging device in a mobile radiographic system for portable detectors can include a connector system that can mate (e.g., automatically self-aligns, self-connects and/or self-disconnects) to a grid holder assembly or a portable DR detector and internal circuitry (not shown) can charge an on board battery (e.g., for the grid holder and/or a DR detector) when mounted at the connector system. FIGS. 17A-17C are diagrams that illustrate perspective views of an embodiment of a connector assembly to connect to charge portable detectors in a mobile radiographic system. As shown in FIGS. 17A-17C, a second type electrical connector 1770 can be restrained with the capability of three-dimensional movement for connection to the detector (e.g., corresponding first type electrical connector). The second type electrical connector 1770 can optionally include a first orientation projection 1775a and a second orientation projection 1775b. In one embodiment, the second type electrical connector 770 can be mounted at a housing 1780 attached to mobile radiographic system (e.g., mount or recess). The second type electrical connector 1770 can move in at least one of an x-direction, a y-direction and a z-direction in the housing 1780 (e.g., an air gap). In one embodiment, second type electrical connector 1770 can include at least one electrical connection portion 1772 and at least one alignment portion 1774. As shown in FIGS. 17A-17C, the second orientation projection 1775b can limit movement of the second type electrical connector 1770 in at least a z-direction within the housing 1780 and the first orientation projection 1775a can limit movement in at least the x-direction or the y-direction in the recess 1980. In one embodiment, the connector 1770 can move differing amounts in one or more of the x, y, and z directions.

In one embodiment, the charge system (e.g., charge system 1500) at the mobile radiographic apparatus can couple (e.g., through a transformer) to an external power supply (e.g., outlet in a hospital room) and/or to a power source of the mobile radiographic apparatus. Further, such a charge system can selectively choose the external power source based on a characteristic or condition of the power source of the mobile radiographic apparatus.

In accordance with one embodiment, the invention can provide a mobile radiography apparatus that can include mobile radiography apparatus comprising a moveable transport frame; an adjustable support structure coupled to the moveable transport frame; an x-ray source coupled to the adjustable support structure; and a detector charger device configured to charge a first power source for at least one radiographic detector at the mobile radiography apparatus, where the detector recharge device can include a first radiographic detector charger to charge the first power source for the at least one radiographic detector, and a second radiographic detector charger to charge the first power source for the at least one radiographic detector, where the mobile radiography apparatus can charge the first power source of the at least one radiographic detector selectively using each of the first radiographic detector charger and the second radiographic detector charger. In one embodiment, the first and second radiographic detector chargers can respectively include first and second engagable connectors. In one embodiment, the first radiographic detector charger is configured to charge the first power source when the first power source is removed from the at least one radiographic detector and the second radiographic detector charger is configured to charge the first power source when the first power source is in the at least one radiographic detector. Further, the first radiographic detector charger or the second radiographic detector charger can comprise a mount or a recess at the mobile radiography apparatus, where the second radiographic detector charger is configured to charge the at least one radiographic detector mounted in a grid holder.

Embodiments according to the application can provide a constant source of energy to wireless x-ray devices or detectors used in electronic image capture for mobile medical diagnostic imaging. Wireless devices depend primarily on DC power supplied by batteries. Embodiments according to the application can charge batteries while being stored in the mobile radiographic cart to provide or insure on demand imaging. Recharging batteries can also reduce or eliminate a need for radiography technicians to access the batteries for replacement.

Embodiments according to the application can include a passive electrical connector system that can automatically mate (e.g., self-aligns, self-connects and self-disconnects) to a grid holder assembly for a portable digital radiographic (DR) detector and internal circuitry can charge an on board battery (e.g., for the grid holder and/or a DR detector battery when the DR detector is assembled to the grid holder) when stored (e.g., in a storage area) at a mobile radiographic cart. In one embodiment, a recharge device can include mechanical housings, electrical contacts, and an actuator (e.g., used to insure mating of the connectors). In one embodiment, a system can include one female connector on the grid holder and two male connectors in a storage area, recess, slot or bin of the mobile radiographic cart to insure charging in multiple orientations (e.g., both) of the grid holder when placed into the storage bin. DR detectors and/or grid holder can be charged during transport of the mobile radiographic cart. Embodiments according to the application can include additional passive electrical connector system that can charge one or more batteries removed from a DR detector in additional storage slots of a mobile radiographic cart. Removed DR detector batteries can be charged during transport of the mobile radiographic cart.

In one embodiment, a storage area can include a detector charge device where a self-align electrical connector system can include a restrained extendable magnetic tether connector on one of the grid holder assembly and storage slot of the mobile radiographic cart and a fixed corresponding connector on the other of the grid holder assembly and the storage slot. Alternatively, a storage area can include a detector charge device with a self-aligning electrical connector system between a grid holder and restrained extendable connector using levers and springs, mechanical linkages, pneumatics (e.g., air or hydraulic), or electromechanical (e.g., motors, solenoids) actuators to mate an electrical male/female connector pairing when the grid holder assembly is stored at the mobile radiographic cart.

Exemplary embodiments according to the application can include various features described herein (individually or in combination).

In one embodiment, a grid holder assembly can include a handle at one end, which can reduce a number of positions that the grid holder assembly can be placed in a storage area to two positions (e.g., DR detector face up or DR detector face down). The grid holder assembly can include a first type electrical connector to be mated to one of a plurality of second type electrical connectors positioned at a storage area for the grid holder assembly on a mobile radiographic cart. The first type electrical connector can be exposed in an exterior surface (e.g., a side surface, a back surface or an end surface) of the grid holder assembly. A charge system for the grid holder assembly can include the second type electrical connector mounted with a limited three dimensional movement within a storage slot of the storage area for the mobile radiographic cart. For example, the second type electrical connector can have a limited motion in a side-to-side or lateral direction (e.g., 0.1 to 2 inches), limited motion in a side-to-side or anterior direction (e.g., 0.1 to 2 inches), and/or limited motion in a vertical direction (e.g., 0.1 to 2 inches). Preferably, such limited three dimensional movement allows the second type electrical connector to automatically attach to the first type electrical connector when the grid holder assembly is mounted (e.g., locked) in the storage area. In one embodiment, the alignment between the first type and second type connector can be implemented using magnetic fields. For example, the first type electrical connector can include a first plurality of oriented magnets that correspond (e.g., N pole to S pole) to a second plurality of magnets at the second type electrical connector. In this case, when the first type electrical connector is near or close to ((e.g., 0.1 to 2 inches) the second type electrical connector, a magnetic force between the first and second plurality of magnets can align and attach the movable second type electrical connector into electrical connection with the first type electrical connector. Engagement and/or disengagement of the first type electrical connector to the second type electrical connector can be sensed by a sensor in the mobile radiographic cart (e.g., connector housing) and indicated by visual (e.g., light on cart, light on grid holder assembly, or indication on a display screen) and/or audible indication.

In one embodiment, a handle of the grid holder assembly can be used by a technician to reciprocally store and remove the grid holder assembly from the storage slot of the storage area of the mobile radiographic cart. A mechanical stop or restricting bar can be within a connector housing to restrain the second type electrical connector for detaching from the grid holder assembly (e.g., first type electrical connector) when the technician removes the remove the grid holder assembly from the storage slot of the storage area of the mobile radiographic cart.

In one embodiment, the slot for the grid holder assembly can have a decreasing cross-sectional size to guide the grid holder to a selected or desired position while the grid holder is moving from a first position (e.g., FIG. 4A) outside the mobile radiographic cart to a second stored position at the mobile radiographic cart (e.g., FIGS. 14A, 14B). The slot for the grid holder assembly can include a vertically extending guide bar along one side edge to urge the grid holder assembly to the second position as the grid holder assembly travels or descends from an opening toward a bottom surface of the slot. For example, the guide bar can be spring loaded or use friction between opposing sides of the slot and sides of the grid holder assembly to reduce a speed of the grid holder assembly into the slot. In one embodiment, the friction or pressure can increase (e.g., linearly or non-linearly) as the grid holder assembly travels closer to the charging position or bottom of the storage/charging slot. Alternatively, the friction can be sufficient that the operator has to push slightly to get the grid holder assembly to the charging position or bottom of the storage/charging slot.

In one embodiment, the storage/charging slot for charging the grid assembly holder can include a suspension mechanism or cushioning mechanism to reduce an impact to the grid holder assembly when being moved to the charging position or bottom of the storage/charging slot. In one embodiment, a suspension mechanism can be suspension bar where the connector housing to for the second type electrical connector can be mounted at, attached to or part of the suspension bar.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A mobile radiography apparatus comprising:
a transport frame configured to roll across a surface;
an adjustable support attached to the transport frame, one end of the adjustable support configured to be horizontally and vertically moveable;
an x-ray source coupled to the one end of the adjustable support; and
an x-ray detector recharge device attached to the transport frame, the recharge device comprising a first storage slot configured to receive and charge a first portable x-ray detector having a first chargeable power source, the first storage slot comprising a decreasing cross-sectional area to increase frictional resistance against the first detector as the first detector is inserted into, and moved toward a bottom of, the first storage slot,
wherein the recharge device includes an electrical recharge connector at the bottom of the first storage slot, the first detector includes an electrical charging connector on a bottom facing side of the first detector, and wherein the charging connector is configured to electrically engage the recharge connector when the first detector is fully inserted into the first slot, and
wherein at least one of the electrical recharge connector and the electrical charging connector is moveable in two-dimensions or in three-dimensions to facilitate electrical engagement therebetween when the first detector is fully inserted into the first slot, wherein the two-dimensions and the three-dimensions include at least two orthogonal directions.

2. The apparatus of claim 1, wherein the first storage slot includes elastic members to increase the frictional resistance.

3. The apparatus of claim 1, wherein the recharge device further comprises a second storage slot configured to receive and charge a second portable x-ray detector having a second chargeable power source, the second x-ray detector comprising a smaller size than the first x-ray detector, the second storage slot comprising a decreasing cross-sectional area to increase frictional resistance against the second detector as the second detector is inserted into, and moved toward a bottom of, the second storage slot, the second storage slot comprising a size that is smaller than a size of the first storage slot to prevent insertion of the first x-ray detector therein.

4. The apparatus of claim 3, wherein the first and second storage slots each comprise a width, a length, and a depth, and wherein at least one of a width, a length, and a depth of the second storage slot is less than a corresponding width, length, and depth of the first storage slot to prevent insertion of the first x-ray detector therein.

5. The apparatus of claim 3, wherein the recharge device further comprises a third storage slot sized to receive a third detector, the third detector comprising a smaller size than the first and the second detectors, the third storage slot comprising a size that is smaller than the size of the first and the second storage slots to prevent insertion of the first x-ray detector and the second x-ray detector therein.

6. The apparatus of claim 5, wherein the first chargeable power source is configured to be removable from the first detector, and wherein the recharge device further comprises a fourth storage slot configured to receive and recharge the removable first chargeable power source when the removable first chargeable power source is fully inserted therein.

7. The apparatus of claim 1, wherein the first chargeable power source is configured to be removable from the first detector, and wherein the recharge device further comprises a second storage slot configured to receive and recharge the removable first chargeable power source when the removable first chargeable power source is fully inserted therein.

8. A mobile radiography apparatus comprising:
a transport frame configured to roll across a surface;
an adjustable support attached to the transport frame, one end of the adjustable support configured to be horizontally and vertically moveable;
an x-ray source coupled to the one end of the adjustable support; and
an x-ray detector recharge device attached to the transport frame, the recharge device comprising a plurality of different sized storage slots each configured to receive and charge one of a plurality of different sized x-ray detectors inserted therein, each of the x-ray detectors comprising a chargeable power source, a first one of the storage slots sized to receive only one of the plurality of different sized detectors and to prevent insertion of remaining ones of the plurality of different sized detectors, wherein the first one of the storage slots includes a height or a width smaller than a corresponding height or width of the remaining ones of the plurality of different sized detectors,
wherein said plurality of storage slots each comprises an electrical recharge connector at a bottom of the storage slot, the plurality of different sized x-ray detectors each include an electrical charging connector on a bottom facing side thereof, and wherein each of the charging connectors is configured to electrically engage a corresponding one of the recharge connectors when the x-ray detectors are fully inserted into the storage slots, and
wherein at least one of the electrical recharge connectors and the electrical charging connectors is moveable in two-dimensions or in three-dimensions to facilitate electrical engagement therebetween when the x-ray detectors are fully inserted into the storage slots, wherein the two-dimensions and the three-dimensions include at least two orthogonal directions.

9. The apparatus of claim 8, wherein said plurality of storage slots each comprises a decreasing cross-sectional area configured to increase frictional resistance against a detector inserted therein as the inserted detector is moved toward a bottom of the storage slot.

10. The apparatus of claim 9, wherein said plurality of storage slots each comprises elastic members to increase the frictional resistance.

11. The apparatus of claim 9, wherein the chargeable power sources are each configured to be removable from the detectors, and wherein the recharge device further comprises a plurality of battery storage slots each configured to receive and recharge one of the removable chargeable power sources when the removable chargeable power sources are fully inserted therein.

12. A mobile radiography apparatus comprising:
a transport frame configured to roll across a surface;
an adjustable support attached to the transport frame, one end of the adjustable support configured to be horizontally and vertically moveable;
an x-ray source coupled to the one end of the adjustable support; and
an x-ray detector recharge device attached to the transport frame, the recharge device comprising a storage slot configured to receive a first grid holder, the first grid holder configured to secure therein a first portable x-ray detector and to secure therein a second portable x-ray detector after the first portable x-ray detector is removed from the first grid holder, the first and second portable x-ray detectors each configured to be manually mounted in and manually removed from the first grid holder, the first x-ray detector having a first chargeable power source configured to be charged through the first grid holder when the first grid holder is fully inserted into the storage slot, the second x-ray detector having a second chargeable power source configured to be charged through the first grid holder when the first grid holder is fully inserted into the storage slot,
wherein the recharge device includes an electrical recharge connector at the bottom of the storage slot, the first grid holder includes an electrical grid charging connector on a bottom facing side thereof, the electrical grid charging connector electrically connected to an electrical detector connector on an interior facing portion of the first grid holder, the first detector includes an electrical detector charging connector on a side of the first detector that faces the electrical detector connector, the detector charging connector is configured to electrically engage the detector connector when the first detector is secured in the first grid holder, wherein the grid charging connector is configured to electrically engage the recharge connector when the first grid holder is fully inserted into the storage slot, and wherein the electrical detector charging connector is not capable of electrically engaging the electrical recharge connector,
wherein at least one of the electrical grid charging connector and the electrical recharge connector is moveable in two-dimensions or in three-dimensions to facilitate electrical engagement therebetween when the first grid holder is fully inserted into the storage slot, and wherein the two-dimensions and the three-dimensions include at least two orthogonal directions.

13. The apparatus of claim 12, wherein the storage slot is further configured to receive a second grid holder having secured therein the second portable x-ray detector, the second chargeable power source is configured to be charged through the second grid holder when the second x-ray detector is electrically engaged with the second grid holder and when the second grid holder is fully inserted into the storage slot, the second x-ray detector comprises a size different than the first x-ray detector, and wherein the second x-ray detector is not capable of electrically engaging the electrical recharge connector.

* * * * *